United States Patent [19]

Grögler et al.

[11] Patent Number: 4,667,008

[45] Date of Patent: May 19, 1987

[54] PROCESS FOR THE PRODUCTION OF SOLID POLYISOCYANATES OF RETARDED REACTIVITY, POLYMER-COATED, FINELY DIVIDED POLYISOCYANATES AND THEIR USE

[75] Inventors: Gerhard Grögler, Leverkusen; Richard Kopp, Cologne; Heinrich Hess, Leverkusen, all of Fed. Rep. of Germany

[73] Assignee: Bayer Aktiengesellschaft, Leverkusen, Fed. Rep. of Germany

[21] Appl. No.: 732,039

[22] Filed: May 8, 1985

[30] Foreign Application Priority Data

May 18, 1984 [DE] Fed. Rep. of Germany ....... 3418429

[51] Int. Cl.$^4$ .................... C08G 18/32; C08G 18/48
[52] U.S. Cl. .......................... 528/67; 528/68; 528/44; 528/85; 428/403; 521/51; 252/188.31
[58] Field of Search .............. 528/67, 68, 44, 85; 428/403; 521/51; 252/188.31

[56] References Cited

U.S. PATENT DOCUMENTS

| | | | |
|---|---|---|---|
| 2,800,457 | 7/1957 | Green et al. | 252/316 |
| 3,409,461 | 11/1968 | Mehlo | 117/100 |
| 3,475,200 | 10/1969 | Kallert et al. | 117/94 |
| 3,489,744 | 1/1970 | Schwarcz et al. | 260/239 |
| 3,551,346 | 12/1970 | Breen et al. | 252/316 |
| 4,076,774 | 2/1978 | Short | 264/4 |
| 4,120,518 | 10/1978 | Baatz et al. | 282/27.5 |
| 4,251,427 | 2/1981 | Recker et al. | 260/37 N |
| 4,379,071 | 4/1983 | Schnoring et al. | 252/316 |
| 4,400,497 | 8/1983 | Blum et al. | 528/45 |
| 4,405,952 | 9/1983 | Slakmon | 360/49 |
| 4,483,974 | 11/1984 | Grogler et al. | 528/68 |

FOREIGN PATENT DOCUMENTS

| | | |
|---|---|---|
| 2557407 | 6/1977 | Fed. Rep. of Germany . |
| 3228723 | 2/1984 | Fed. Rep. of Germany . |
| 3228724 | 2/1984 | Fed. Rep. of Germany . |
| 3228670 | 2/1984 | Fed. Rep. of Germany . |
| 1103202 | 2/1968 | United Kingdom . |

*Primary Examiner*—John Kight
*Assistant Examiner*—M. L. Moore
*Attorney, Agent, or Firm*—Gene Harsh; Joseph C. Gil

[57] ABSTRACT

This invention relates to the production of polymer-coated, finely divided polyisocyanates by mixing (A) solid, finely divided polyisocyanates (preferably dimeric diisocyanates or urea diisocyanates) with (B) polyisocyanates differing in composition from those mentioned under (A) (preferably (cyclo) aliphatic polyisocyanates, such as biuretized diisocyanates or trimers or NCO-prepolymers), in quantities of from 0.05 to 50 parts by weight, and preferably in quantities of from 0.2 to 25 parts by weight, of (B) per 100 parts by weight of (A). The solid polyisocyanate particles surface-modified by covering with polyisocyanates (B) and then reacted with (D) isocyanate-reactive compounds containing reactive hydrogen atoms or with compounds free from active hydrogen atoms which form polymers with isocyanates in sub-equivalent to substantially equivalent quantities (preferably 0.5 to 1.0 equivalent per NCO-equivalent), in the presence of (C) inert, weakly polar organic solvents, (for example aliphatic hydrocarbons or relatively long chain dialkyl ethers), plasticizers, polyols or aromatic polyamines.

A polymer coating is formed by the reaction of (B) and (D) around the solid polyisocyanate cores (A).

The present invention also relates to the polyisocyanate particles covered with polyisocyanates (B) on the surface of the solid polyisocyanates (A) and, in particular, to the foreign-polymer coated, finely particulate polyisocyanates of retarded reactivity obtained by reaction with (D).

The present invention also relates to the use of the polyisocyanate-covered and, more particularly, polymer-coated polyisocyanates, optionally in suspension in polyols and/or plasticizers, for the production of polyurethanes, more particularly in one-component polyurethane reactive systems having a long shelf life and a high thickening point.

9 Claims, No Drawings

PROCESS FOR THE PRODUCTION OF SOLID POLYISOCYANATES OF RETARDED REACTIVITY, POLYMER-COATED, FINELY DIVIDED POLYISOCYANATES AND THEIR USE

BACKGROUND OF THE INVENTION

Hitherto, very little literature has been published on the surface modification of polyisocyanates which are solid at room temperature.

German Offenlegungsschrift No. 2,557,407 describes a process in which a solution of a polyisocyanate in a low-boiling solvent is sprayed into a reactor with gaseous di- and/or polyamine. Hollow beads of polyurethane polyurea (which are preferably used as fillers) are obtained by the reaction of the polyisocyanate with the amine and by evaporation of the solvent. The reaction is generally conducted in such a way that the NCO-groups react off completely with the amine and any other NCO-reactive components (for example diols) added.

U.S. Pat. No. 3,409,461 describes the coating of polyisocyanates with a protective substance, preferably a polymer, to deactivate the polyisocyanate particles at their surface. The isocyanate is dispersed in a solution of the polymer in a low-boiling solvent which has very little dissolving effect on the isocyanate. The dispersion is then spray-dried. Finely ground (particle size 1 to 10 $\mu$m) naphthylene-1,5-diisocyanate is preferably spray-dried with a 1 to 2.5% solution of polystyrene, polyvinyl butyl ether, chlorinated rubber and the like in tetrachloromethane. Free-flowing powders having particle sizes of from about 1 to 50 $\mu$m are obtained. These powders are suitable for improving the adhesion of polyester products (woven fabrics, fibers, films) to rubber elastomers. In this process for coating isocyanates with added polymers from solution, considerable quantities of solvents (which may be toxic) have to be used (for example 4 kg of tetrachloromethane for 50 g of naphthylene-1,5-diisocyanate) and then removed again in an energy-consuming operation. One particular disadvantage of the process lies in the high percentage of coating material (from 9 to 91% by weight; in the Examples, it is generally of the order of 50% by weight) in the total weight of the coated isocyanate. As a result of this, an excessive proportion of troublesome foreign substance would have to be introduced in the production of high-quality polyurethanes.

U.S. Pat. No. 3,551,346 describes the encapsulation of liquid diisocyanates by interfacial reactions of $CH_3$—Si—$(OCH_3)_3$ dissolved in the diisocyanate with $(CH_3)_3$.Si—O—Na dissolved in the aqueous phase to form a film. These droplets preencapsulated by silicone polymer formation are then "encapsulated" by coacervation (for example with oppositely charged polymers in accordance with U.S. Pat. No. 2,800,457).

German Offenlegungsschrift No. 2,311,712 describes a process for the encapsulation of solid substances by a polymer shell formed from NCO-prepolymers and chain-extending agents. The reactive mixture and an aqueous phase are introduced into a zone of high turbulence at a temperature at which all the reactants are liquid. Microcapsules are formed through the formation of a high moleculare weight polymer as the coating material (for example a polyurea of NCO-prepolymers and polyamines). This known process may be used to encapsulate any solids or liquids which are inert to the NCO-prepolymers and the chain-extending agents (and water) and are insoluble in water (for example trischloroethyl phosphate flameproofing agents, plasticizers, fragrances, etc.). Similar processes are described, for example, in U.S. Pat. No. 4,120,518 for encapsulation reactions with carbodiimide-containing polyisocyanates to form the filling.

German Offenlegungsschrift No. 1,570,548 describes a one-component system of relatively long shelf-life consisting of a mixture of (i) 1 moles of a polyester, polyether or polythioether, (ii) at least 1.5 moles of a solid isocyanate containing uret dione groups and having a melting point of 100° C. or more and (iii) at least 0.3 mole of a solid chain-extending agent containing OH- and/or $NH_2$-groups and having a melting point of 80° C. or more. At least 80% of the solid constituents of the mixture are required to have a particle size of 30 $\mu$m or less. The shelf life of this one-component system amounts to between a few days and a few weeks at room temperature, but only to a few hours at 50° C. One disadvantage of this known process is that at least two of the three reactants have to be present in the solid form to guarantee the requisite shelf life. The effect of this is that the mixtures obtained generally have very high viscosities and their viscosities continue to increase slowly because none of the compounds has been adequately modified in its reactivity. The reaction at the surface of the solid particles, which is reflected in the steady increase in viscosity, takes place uncontrolled and too slowly in practice and does not sufficiently retard the reactivity of the polyisocyanates to the point where the system is self-stabilizing. In addition, when the mixture is hardened, inhomogeneities are inevitable in the fully heated product due to the high percentages of solid constituents. Processing of the highly viscous to solid mixtures is also more difficult because, in contrast to liquid mixtures, they first have to be brought into a formable condition either by increasing temperature or by applying pressure.

Comparative tests have shown that, when high-melting polyisocyanates are mixed with relatively high molecular weight and low molecular weight polyols, a constant and relatively rapid reaction takes place with a marked increase in viscosity. In other words, the surface reaction on the solid polyisocyanate particles does not form a coating around the polyisocyanate which is sufficient for retarding, i.e. has an adequate stabilizing effect.

British Patent No. 1,134,285 describes a process for the production of dimeric diisocyanates in an aqueous reaction medium. According to this reference, dimeric diisocyanates produced in this way do not react with polyfunctional compounds containing reactive hydrogen atoms at room temperature, although mixtures with polyols may be thermally crosslinked to form polyurethanes. Stability may possibly be brought about by a slow surface reaction of isocyanate groups with water. Crosslinking is then brough about at high temperatures, for example 150° to 200° C., by cleavage of the uret dione ring.

Storable reactive systems having long pot lives are described in German Offenlegungsschriften Nos. 2,842,805 and 2,941,051. According to these references, polyisocyanate mixtures of high-melting polyisocyanates (for example dimeric TDI) and liquid polyisocyanates are mixed with relatively high molecular weight and low molecular weight polyols, optionally in the presence of subequivalent quantities of a compound containing from 2 to 4 amino groups (for example cycloaliphatic diamines or triamines, hydrazine and subsituted hydrazines or acid hydrazides), to form a dispersion-stable system which, in a second stage, is hardened in molds at temperatures above 90° C., optionally after the addition of glass fibers.

Polyisocyanates stabilized with subequivalent quantities (0.01 to 20 or 25% of the NCO-groups present) of diamines and other NH-functional compounds in admixture with polyols, polyamines or polyhydrazides are also described in German Offenlegungsschriften Nos. 3,112,054 (which corresponds to U.S. Pat. No. 4,400,497). 3,228,723, 3,228,724, 3,228,670 and 3,230,757 (which corresponds to U.S. Pat. No. 4,483,974). The polyisocyanate particles are thus deactivated at their surface with up to 25 equivalent percent of all the NCO-groups present to form a polymer (for example polyurea) coating. Dispersions of deactivated polyisocyanate particles such as these in polyols and/or polyamines, show at least very good stability in storage at room temperature. It is only above a solidification or thickening temperature that the reactive system enters into polyurethane(urea)-forming reactions and, in that case, forms elastomers or similar end products.

As already observed in German Offenlegungsschrift No. 3,230,757, the compounds used for the surface reaction (for example the aliphatic polyamines), generally do not react off completely—largely irrespective of the quantity of amine—if they are reacted in dispersion in polyols or polyamines. Thus, part of these polyamines remains unreacted in the reactive dispersion. This can occasionally produce a desirable effect insofar as any surface defects in the polyurea coating which may begin to form during storage or handling of the reactive mixture are cured again ("self-healing effect") so that stability in storage remains unaffected.

On the other hand, however, this effect involves a serious disadvantage where it is attempted to produce relatively large (large-volume) moldings. This is because it has been found that, during the slow heating of reactive systems (due to the poor transfer of heat in the molding or in the event of prolonged heating to temperatures just below the thickening point of the system, which can often be necessary to improve the pourability of the systems) or after partial solidification on the hot outer mold, the still liquid reactive dispersion core containing unreacted amine stabilizer is further deactivated so that the thickening temperature in the core continues to increase. This gives rise to the formation of inhomogeneous bubbles. In addition, the liquid core can break the skin open and leak out, thus damaging the surface. Accordingly, the strength of inhomogeneous moldings such as these is unsatisfactory.

Another disadvantage of the known stabilizing process lies in the fact that, if the unreacted stabilizer component remaining in the dispersion is removed, the stability of the dispersions in storage is often distinctly reduced or even lost altogether.

For this reason, it is not possible to stabilize a polyisocyanate in isocyanate-reactive compounds (for example polyols) in accordance with the prior art by surface modification of the polyisocyanate particles with a stabilizing component (for example an aliphatic diamine), and then to carry out reactions between the isocyanate-reactive compounds and standard liquid polyisocyanates in order to obtain preextension of a long-chain polyol which may be necessary to obviate viscosity problems or to obtain some degree of thixotropy. In most cases, the liquid polyisocyanate added normally destabilizes the dispersion.

In addition, where aliphatic diamines are used as the stabilizing component ("amine stabilizer"), the addition of compounds which are reactive to, or absorb, aliphatic diamines (such as for example halogen-containing flameproofing agents and blowing agents, zeolites, fatty acids, phosphoric acid esters, and certain solvents) is not recommended and, in some cases, is impossible. The same also applies to deactivating agents of other chemical types.

According to the references mentioned above, stabilization of the polyisocyanate by reacting the isocyanate particles with a stabilizing component may even be carried out before mixing with the isocyanatereactive compounds by reacting the polyisocyanate with the stabilizing component in an inert solvent which does not dissolve the polyisocyanate, followed by isolation, so that no unreacted "amine stabilizer" component is present in the polyisocyanate. However, this brings another disadvantage of the known process. Because no excess deactivating component is present where this solid polyisocyanate deactivated by a preliminary reaction is used, the dispersions containing isocyanate-reactive compounds prepared with the solid deactivated polyisocyanate are no longer self-healing and are highly susceptible to mechanical and/or thermal influences.

Another disadvantage of the known stabilizing process is that up to 25 equivalent percent of the solid (generally very expensive) polyisocyanate component is used up during stabilization and is no longer available for further polyurethane reactions.

DESCRIPTION OF THE INVENTION

The object of the present invention is to provide polyisocyanate particles of retarded reactivity which still contain their NCO-groups in reactive form in the solid polyisocyanate, but which are modified by a covering of other, preferably liquid or oily to resinous polyisocyanate which is easy and safe to apply. These covered isocyanates are reacted with polymer-forming reagents, and form a polymer coating which enables their reactivity to be safely retarded. Accordingly, reactive polyurethane mixtures characterized by high stability in storage and polyurethane formation are obtainable in this way. In addition, it is possible to obtain reactive systems which do not undergo a steady increase in thickening point when used for the production of moldings of large volume.

Accordingly, the present invention relates to a process for the production of solid polyisocyanates stabilized by a polymer coating and showing retarded reactivity, comprising (I) mixing
  (A) at least one solid polyisocyanate in particulate form (preferably dimeric or trimeric diisocyanates or urea diisocyanates, and particularly those of aromatic structure) having a melting point above 38° C., more preferably, having a melting point,
  (B) at least one polyisocyanate having a composition different from that of component (A) and being in a form capable of covering the particles of component (A) in quantities of from 0.50 to 50 parts by weight, preferably in quantities of from 0.2 to 25 parts by weight and, more preferably, in quantities of from 1 to 12 parts by weight of (B) to 100 parts of (A).

said mixing being conducted at a temperature below the melting point of component (A), the component (B) optionally being dissolved or emulsified in (C) and resulting in the covering of the particles of component (A) by component (B), and (II) reacting the resultant covered product suspended in
   (C) a component selected from the group consisting of (i) inert, weaking polar organic solvents (and more particularly aliphatic hydrocarbons and/or relatively long-chain dialkyl ethers), (ii) plasticizers, (iii) organic compounds containing two or more hydroxyl groups and having molecular weights of from 400 to 6000, (iv) organic compounds containing two or more aromatically bound amino groups preferably aromatically bound and having molecular weights of from 400 to 6000, and (v) mixtures thereof, with
   (D) at least one component selected from the group consisting of (i) compounds containing one or more hydrogen atoms capable of reacting with isocyanate groups, (ii) compounds containing no hydrogen atoms capable of reacting with isocyanate groups but which are capable of forming polymers with isocyanates, and (iii) mixtures thereof, provided that component (D) cannot be of the type included within the definition of component (C).
in substantially equivalent quantities (referring to the equivalents of (D) versus equivalents of (B)) (preferably from 0.5 to 1.0 equivalent per NCO-equivalent), wherein said reaction results in the coating of component (A) by a polymer formed by the reaction of components (B) and (D).

The present invention also relates to the polyisocyanate particles covered over the surface of the finely divided polyisocyanates (A) with from 0.05 to 50 parts by weight of other polyisocyanates (B) and to their use in the production of polyurethanes.

More particularly, the invention relates to the polymer-coated, finely divided polyisocyanates (E) of retarded activity obtainable by the process according to the invention, i.e. by reacting the solid polyisocyanate particles coated with other polyisocyanates (B) with NCO-reactive compounds (D), optionally in suspension in relatively high molecular weight polyols and/or relatively high molecular weight aromatic polyamines, preferably in combination with low molecular weight polyols and/or aromatic diamines.

The present invention also relates to the use of the polymer-coated polyisocyanates (E) obtainable in accordance with the invention (optionally in suspension in polyols and/or polyamines and/or plasticizers) for the production of polyurethanes, preferably in one-component reactive polyurethane (PU) systems having a long shelf life and a high thickening point, which form polyurethanes under the effect of heat and/or mechanical energy and/or polar solvents, and more particularly for the production of elastomers, cellular polyurethanes, sealing compounds and adhesives.

The present invention also relates to the use of polymer-coated, stabilized, solid polyisocyanates of retarded reactivity obtainable by the described processes (optionally in suspension in low molecular weight and/or relatively high molecular weight polyol and/or low molecular weight and/or relatively high molecular weight aromatic polyamino compounds and/or relatively high molecular weight aliphatic polyamino compounds) as polyisocyanate component and, optionally, relatively high molecular weight polyol and/or polyamino compounds and, optionally, low molecular weight chain-extending agents for the production of polyurethanes, preferably for the production of polyurethanes via storable one-component reactive systems. It is preferred to suspend the polymer coated polyisocyanates (E) in higher molecular polyhydroxy compounds. Such a suspension can be formed by suspending the solid polyisocyanates (A) in higher molecular polyols, covering with liquid, oily or in (C) dissolved or emulsified polyisocyanates (B) and reacting with (D), optionally dissolved in (C), to form the polymer coated polyisocyanates (E), suspended in the polyols. (C) in this case is selected from the group of polyols or inert, weakly polar solvents. If (C) are inert, weakly polar solvents, these solvents can be distilled off (preferably in vacuo) towards the end of the process.

The one-component systems can be in the form of free-flowing or low melting reactive systems having a thickening temperature of 55° C. or more which are hardened by heat, shear forces and/or polar solvents to form solid or cellular polyurethanes.

The polyisocyanates or reactive systems according to the invention do not have any of the above-mentioned disadvantages of the prior art. The invention avoids the disadvantages of the prior art in that the solid polyisocyanates (A) are not deactivated by the reaction at their surface with deactivating components, in which up to 25 equivalent percent of the NCO-groups of the solid polyisocyanates (A) are used up. Instead of polymer coating of component (D) and a polyisocyanate (B) different from the solid polyisocyanate (A) is formed. The polyisocyanate (B) is initially applied as a "covering" to the solid polyisocyanate (A) and adsorbed or absorbed thereon. The coating polymer is a "foreign polymer" of (B) and (D) as opposed to the known polymer coating of a polyurea of (A) and (D).

Since the two components (B) and (D) for forming the polyurea or polymer coating react off completely, no problems arise through subsequent variation of the coating around the solid polyisocyanate. In other words, the thickening point remains constant, even in the event of slow heating at elevated temperatures and even in the production of moldings of large volume.

Studies conducted hitherto have shown that the thickening point is generally not as dependent upon the quantity of the polyurea coating formed as in the case where stabilization is carried out in known manner, i.e. solely by a surface reaction with an aliphatic polyamine.

Since no more components capable of participating in the reaction are present after formation of the polyurea coating, further reactions with any of the components normally used in polyurethane chemistry are possible even after the stabilizing and deactivating reaction. For example, pre-extension of a polyether polyol, optionally used as the polyol, may be carried out after the stabilizing reaction by the addition of liquid diisocyanates and catalysts.

It is even possible to use auxiliaries and additives which cannot be used in state-of-the-art storable systems, such as, for example, halogen-containing flame-proofing agents, acid anhyrides, fatty acids, carbodiimides, phosphates and phosphites or zeolites.

Solid polyisocyanates may also be stabilized in accordance with the invention in an inert solvent which does not dissolve the solid polyisocyanate, in which case the stabilized polyisocyanates obtained are interesting starting materials not only for the dispersions according to the invention. These solid, coated polyisocyanates show increased stability in storage in the production of storable dispersions by comparison with the polyisocyanates stabilized by known methods.

The polymer coating also differs from the prior art in the fact that it has a different composition ("foreign polymer coating") from a polymer formed from the polyisocyanate (A)-core itself.

Surprisingly, the polymer coating is formed particularly favorably with aliphatic polyisocyanates as the covering polyisocyanate (B) although the reactivity of aliphatic NCO-groups is known to be lower than that of aromatic NCO-groups.

Suitable starting components for the solid finely divided polyisocyanates (A) stabilized in accordance with the invention are any di- or polyisocyanates or mixtures thereof, providing they have a melting point above 38° C., preferably above 70° C. and, more preferably, above 110° C.

These di- or polyisocyanates may be aliphatic, cycloaliphatic, araliphatic, aromatic and heterocyclic polyisocyanates. Aromatic isocyanates are preferred. Also useful are polyphenyl polymethylene polyisocyanates obtained by phosgenating aniline-formaldehyde condensates in accordance with British Patent Nos. 874,430 and 848,671; perchlorinated aryl polyisocyanates; polyisocyanates containing carbodiimide groups; polyisocyanates containing allophanate groups; polyisocyanates containing isocyanurate groups; polyisocyanates containing urethane or urea groups; polyisocyanates containing acylated urea groups; polyisocyanates containing biuret groups; polyisocyanates produced in telomerization reactions; polyisocyanates containing ester groups; and, preferably diisocyanates containing uretdione groups and diisocyanates containing urea groups. The following are examples of suitable polyisocyanates:

| | M.p.: |
|---|---|
| 1,5-diisocyanato-methyl naphthalene | 88–89° C. |
| 1,4-phenylene diisocyanate | 94–96° C. |
| 1,3-dimethylbenzene-4,6-diisocyanate | 70–71° C. |
| 1,4-dimethylbenzene-2,5-diisocyanate | 76° C. |
| 1,4-dichlorobenzene-2,5-diisocyanate | 134–137° C. |
| 1-methoxybenzene-2,4-diisocyanate | 75° C. |
| 1-methoxybenzene-2,5-diisocyanate | 89° C. |
| 1,3-dimethoxybenzene-4,6-diisocyanate | 125° C. |
| azobenzene-4,4'-diisocyanate | 158–161° C. |
| diphenylether-4,4'-diisocyanate | 66–68° C. |
| diphenyl-dimethylmethane-4,4'-diisocyanate | 92° C. |
| naphthalene-1,5-diisocyanate | 127–130° C. |
| 1,4-bis-(1'-methyl-1'-isocyanato)-ethylbenzene (tetramethyl-p-xylylene diisocyanate) | 72° C. |
| 3,3'-dimethylbiphenyl-4,4'-diisocyanate | 68–69° C. |
| diphenylsulfone-4,4'-diisocyanate | 154° C. |
| 4,4'-diisocyanato-(1,2)-diphenylethane | 88–90° C. |
| dimeric 1-methyl-2,4-phenylene diisocyanate | 156° C. |
| dimeric 1-isopropyl-2,4-phenylene diisocyanate | 125° C. |
| dimeric 1-chloro-2,4-phenylene diisocyanate | 177° C. |
| dimeric 2,4-diisocyanatodiphenylsulfide | 178–180° C. |
| dimeric diphenylmethane-4,4'-diisocyanate | |
| 3,3'-diisocyanato-4,4'-(or -2,2')-dimethyl-N,N'—diphenyl urea, | |
| N,N'—bis-[4-(4-isocyanatophenylmethyl)-phenyl]-urea, | |
| N,N'—bis-[4-(2-isocyanatophenylmethyl)-phenyl]-urea, | |
| trimeric 2,4-diisocyanatotoluene)-isocyanurate-isocyanate, | |
| trimeric 4,4'-diisocyanatodiphenylmethane-(isocyanurate-isocyanate), | |
| trimeric isophorone-diisocyanate-(isocyanurate-isocyanate) (cf. DE-OS 2,806,731) | |
| or the adduct of 3 moles of 2,4-diisocyanatotoluene with 1 mole of trimethylol propane. | |

Dimeric urea diisocyanates corresponding to German Offenlegungsschrift 32 32 736 (U.S. application Ser. No. 526,245 (7/1983)) are also suitable, as are mixed trimers based, for example, on TDI/MDI, TDI/HDI (cf. German Offenlegungsschrift No. 3,033,860) or products corresponding to German Offenlegungsschrift No. 3,041,732 to the extent they are solid at temperatures of 38° C. or more.

According to the invention, it is preferred to use dimeric and trimeric diisocyanates and urea diisocyanates. Specific prepared examples include 3,3'-diisocyanato-4,4'-dimethyl-N,N'-diphenylurea; dimeric 2,4-diisocyanatotoluene; dimeric 4,4'-diisocyanatodiphenylmethane and 3,3'-dimethyl-4,4'-diisocyanatodiphenylmethane; and isocyanurates (trimers) based on 2,4-diisocyanatotoluene. The dimeric and trimeric diisocyanates may also be produced in finely divided form by in situ dimerization or trimerization and the urea diisocyanates produced in finely divided form in situ by aqueous reaction. The "in situ" reaction may be conducted in plasticizers, solvents or polyols. The resultant isocyanates are preferably subjected to the coating by component (B) in that finely divided form (because they do not have to be isolated and mechanically size-reduced beforehand). The particle size of (A) is generally in the range from 0.5 to 200 μm and preferably in the range from 1 to 50 μm.

Polyisocyanates differing in composition from the polyisocyanates (A) are used as the polyisocyanates (B) for covering the surface of the solid, finely divided polyisocyanates (A). The polyisocyanates (B) are preferably liquid, oily or, resinous polyisocyanates and, in particular, polyisocyanates of relatively high functionality containing more than two NCO-groups.

It is preferred to use aliphatic or cycloaliphatic difunctional polyisocyanates and, in particular, higher polyisocyanates based on aliphatic or cycloaliphatic isocyanates such as biuretized, dimerized or trimerized polyisocyanates or polyol-modified polyisocyanates or NCO-prepolymers produced with polyols of relatively high molecular weight. Mixtures of the above-mentioned polyisocyanates (B) may also be used.

Examples include hexamethylene diisocyanate, undecamethylene diisocyanate; dimeric acid; di- and polyisocyanates; isophorone diisocyanate; cyclohexane diisocyanates; α,α,α',α'-tetramethyl-m/p-hexahydroxylylene diisocyanates; 4-isocyanatomethyloctane-1,8-diisocyanate; hexahydrotolylene diisocyanates; dicyclohexylmethane diisocyanates; 1,6,11-triisocyanatoundecane; substituted 1,5-diisocyanatopentane derivatives according to European Pat. No. 77,105 (for example 1-methyl-1,5-diisocyanate) or oligomeric derivatives thereof (for example according to European Pat. No. 77,104). It is particularly preferred to use liquid polyisocyanates containing more than two NCO-groups, for example biuret-modified, carbodiimide-modified, trimerized or polyol-modified polyisocyanates, for example, based on hexamethylene diisocyanate, isophorone diisocyante or dicyclohexyl methane diisocyanate. Especially preferred is biuret-modified 1,6-hexane diisocyanate (e.g. Desmodur N from Bayer AG). Aromatic diisocyanates, for example TDI or MDI, are less favorable, although the trimers of TDI and especially NCO-prepolymers, for example from trimethylol propane and TDI, may readily be used in the form of concentrated solutions in toluene or in the form of emulsions in toluene/petroleum ether mixture, since in this form they will form deposits on or will be absorbed on the solid polyisocyanate (A).

Preferred components (C) are inert weakly polar organic solvents and particularly aliphatic or cycloaliphatic hydrocarbons (for example petroleum ether fractions, petrol or cyclohexane) and relatively long-chain dialkyl ethers (preferably $C_3$-$C_8$-alkyl radicals) such as diisopropylether or diisobutyl ether.

In most cases, more strongly polar solvents (for example aromatic hydrocarbons, such as toluene) are unsuitable for use in the sole solvent. They can however be used to form emulsions of (B) by mixing solutions in toluene with petroleum ether or similar non-polar solvents. Relatively long-chain dialkylethers (particularly diisopropylether or diisooctylether) are also particularly favorable solvents.

It has been found that the polyisocyanates (B) are readily deposited onto (A) from, for example, petroleum ether or hexane solutions either by adsorption or even after partial or total evaporation. Accordingly, the solid polyisocyanates (A) are preferably dispersed in aliphatic hydrocarbons or in the above-mentioned ethers, followed by addition of, for example, the polyisocyanates (B) in solution in a small quantity of relatively polar solvents, such as toluene. Component (B) generally precipitates as an oil in the dispersing aliphatic hydrocarbons and is deposited as a covering onto (A) by adsorption. Depending on the solubility of (B), it is possible by carrying out some simple preliminary tests to select solvents or solvent mixtures of the type which enable (A) to be covered with (B). The solvents have to be selected so that they only bring (B) into a dissolved or emulsified phase but leave component (A) in an undissolved, finely divided dispersed phase. The quantity of component (C) is preferably selected so that a stirrable suspension of components (A), (B) and (C) with the reaction of (D) will be obtained. The quantity is usually from 5 to 75 percent by weight and preferably from 10 to 50 percent by weight, based on the total weight of all the components.

It is preferred that the mixing of (A) and (B) occurs in the presence of component (C). The use of the higher molecular weight polyols is also preferred since the resulting product (following reaction with component (D)) can be directly used for the preparation of polyurethanes. The maximum quantity of polyol is normally limited by the equivalence to the NCO-groups to form the polyurethanes.

After the solid polyisocyanate (A) to be coated and the polyisocyanate (B) used for coating have been combined, it may be necessary to wait for a certain time until the polyisocyanate (B) has been absorbed or adsorbed by the solid polyisocyanate (A). In this connection, the use of component (C) can be a crucial factor. It is of advantage to use apolar media such as the above-mentioned aliphatic hydrocarbons, or ethers, (such as diisopropylether) lipophilic plasticizers or polypropylene glycol polyethers, in which the polyisocyanate (B) dissolves relatively poorly and, as a result, deposits more quickly onto the solid polyisocyanate (A).

The quantities of (B) and (A) used amount generally to between 0.05 and 50 parts by weight, preferably to between 0.2 and 25 parts by weight and, more preferably, to between 1 and 12 parts by weight of (B) to 100 parts by weight of (A).

The covering step may also be directly carried out in plasticizers, for example adipic acid dialkyl esters or trialkylphosphates and more particularly long-chain trialkylesters, such as stearyl ester. Proportions of readily volatile, weakly polar solvents (aliphatic hydrocarbons) may also be used and may optionally be removed again after the covering step or after the coating reaction.

For the production of one-component reactive PU mixtures in particular, the polyisocyanates (A) may even be directly dispersed in polyols and surface-covered with (B), optionally after the addition of certain quantities of inert solvents which are subsequently removed. It is less preferred to use more reactive components, such as polyamines for example, as the component (C) during the covering and coating reaction because the polyisocyanates (B) may react with the polyamines to a certain extent.

Following removal of any solvent, the finely divided polyisocyanates covered with (B) are generally free-flowing, non-tacky powder-form solids which are easy to handle. In one variant, the solid polyisocyanate (A) is covered with the dissolved or emulsified polyisocyanate (B). Component (D) is then dissolved in a polyol, and the two are subsequently mixed with one another.

The following classes of compounds may be used as (D) for stabilizing the above-mentioned polyisocyanates:

1. aliphatic or cycloaliphatic di- and polyamines,
2. hydrazine, alkylhydrazines, N,N'-dialkyl hydrazines and di- and polyhydrazide compounds,
3. acyclic, mono- or bicyclic amidines or guanidines without any NCO-reactive hydrogen atoms as described in DE-OS No. 3,403,500
4. mono- or bifunctional amidines or guanidines, one or two groups with NCO-reactive hydrogen atoms,
5. di-, tri- and/or polyols having molecular weights in the range from 62 to 399,
6. other NCO-reactive compounds, such as, for example monoamines, monoalcohols, phenols, oximes, malonic esters, or caprolactam, of the type described in German Offenlegungsschriften Nos. 3,238,670, 3,112,054, 3,228,723 and 3,228,724, or to mixtures thereof.

Di- and poly-aliphatic and/or cycloaliphatic amines are suitable for use as stabilizers, which amines generally have molecular weights of from 60 to about 6000 and preferably from 60 to 3000. Examples include ethylene diamine: 1,2- and 1,3-propane diamine; 1,4-butane diamine; 1,6-hexane diamine; neopentane diamine; 2,2,4- and 2,4,4-trimethyl-1,6-diaminohexane; 2,5-dimethyl-2,5-diaminohexane; 1,10-decane diamine; 1,11-undecane diamine; 1,12-dodecane diamine; bisaminomethyl hexahydro-4,7-methano-indane (TCD-diamine); 1,3-cyclohexane diamine; 1,4-cyclohexane diamine, 1-amino-3,3,5-trimethyl-5-aminomethyl cyclohexane (isophorone diamine); 2,4- and/or 2,6-hexahydrotolylene diamine; 2,4'- and/or 4,4'-diaminodicyclohexylmethane; m- or p-xylylene diamine; bis-(3-aminopropyl)-methylamine; bis-N,N'-(3-aminopropyl)-piperazine; 1-amino-2-aminomethyl-3,3,5-(3,5,5)-trimethyl cyclopentane; 2,2-dialkylpentane-1,5-diamines; or 1,5,11-triaminoundecane; 4-aminomethyl-1,8-diamino-octane; lysine methyl ester; cycloaliphatic triamines according to German Offenlegungsschrift No. 2,614,244; 4,7-dioxadecane-1,10-diamine; 2,4- and 2,6-diamino-3,5-diethyl-1-methylcyclohexane and mixtures thereof; alkylated diaminodicyclohexylmethanes, for example 3,3'-dimethyl-5,5'-diaminodicyclohexylmethane or 3,5-diisopropyl-3',5'-diethyl-4,4'-diaminodicyclohexylmethane; perhydrogenated diaminonaphthalenes; perhydrogenated diaminoanthracenes; diethylene triamine; triethylene tetramine; pentaethylene hexamine; dipropylene triamine; tripropylene tetramine; or N,N'-dimethyl ethylene diamine; 2,5-dimethyl piperazine; 2-methyl piperazine; piperazine (hydrate); 2-hydroxyethyl piperazine and α,α,α',α'-tetramethyl-m/p-xylylene diamine.

In addition to these low molecular weight aliphatic diamines or in admixture therewith, it is also possible to use relatively high molecular weight aliphatic di- and polyamines of the type obtained, for example, by the reductive amination of polyoxyalkylene glycols with ammonia in accordance with Belgian Pat. No. 634,741 or U.S. Pat. No. 3,654,370. Other polyoxyalkylene polyamines of relatively high molecular weight may be obtained by methods of the type described in the booklet entitled "Jeffamine, Polyoxypropylene Amines" published by the Texaco Chemical Co., 1978; by the hydrogenation of cyanoethylated polyoxypropylene glycols (German Offenlegungsschrift No. 1,193,671); by the amination of polypropylene glycol sulfonic acid esters (U.S. Pat. No. 3,236,895); by treating a polyoxyalkylene glycol with epichlorohydrin and a primary amine (French Pat. No. 1,466,708); or by reacting NCO-prepolymers with enamines, aldimines or ketimines containing hydroxyl groups, followed by hydrolysis in accordance with German Auslegeschrift No. 2,546,536. Other suitable aliphatic di- and polyamines of relatively high molecular weight are the polyamines obtainable by the alkaline base hydrolysis of NCO-prepolymers (with aliphatic diisocyanates) via the carbamate stage in accordance with German Offenlegungsschriften Nos. 2,948,419 and 3,039,600. These relatively high molecular weight polyamines have molecular weights of from about 400 to 6000, preferably from 400 to 3000 and, more preferably, from 1000 to 3000. By virtue of their structure, relatively high molecular weight polyamines such as these are particularly suitable for the formation of a non-brittle, elastic polyurea coating. Accordingly, they are used, preferably in admixture with the low molecular weight di- and polyamino compounds, for the stabilization of the covered polyisocyanate particles. Where these relatively high molecular weight amino compounds are used, there is no need for polyols to be added during the stabilizing reaction (to "elasticize" the coating skin around the isocyanate particles).

Other useful "stabilizers" include hydrazine, alkyl hydrazines and N,N'-dialkyl hydrazines, preferably containing $C_1$–$C_6$-alkyl groups, which may even contain chlorine or OH-groups as further substituents (molecular weights preferably in the range from 32 to 198), and/or difunctional or higher, low molecular weight or relatively high molecular weight compounds containing terminal —CO.NH.NH$_2$-groups and having molecular weights of from 90 to about 6000 and preferably from 90 to 3000. Compounds such as these include, for example, hydrazine, generally in the form of hydrazine hydrate; and alkyl substituted hydrazines, for example methyl hydrazine, ethyl hydrazine, hydroxyethyl hydrazine or N,N'-dimethyl hydrazine. Other suitable "stabilizers" are compounds containing terminal hydrazide groups, for example di- or polyhydrazides, such as carbodihydrazide, hydracrylic acid hydrazide, oxalic acid dihydrazide, adipic acid dihydrazide, terephthalic acid dihydrazide and isophthalic acid hydrazide; compounds containing hydrazide and semicarbazide, carbazinic ester or amino groups, for example β-semicarbazido-propionic acid hydrazide, 2-semicarbazido-ethylene carbazinic ester, amino acetic acid hydrazide, β-aminopropionic acid hydrazide; bis-carbazinic esters or bis-semicarbazides, such as ethylene-bis-carbazinic ester or ethylene-bis-semicarbazide or isophorone-bis-semicarbazide. Hydrazine and low molecular weight compounds containing —CO—NH—NH$_2$—groups and having molecular weights of from 32 to 399 are preferred. Hydrazine hydrate, -semicarbazido-propionic acid hydrazide and alkylene-bis-semicarbazides are particularly preferred.

Other particularly favorable stabilizers are acylic, monocyclic or bicyclic compounds containing the amidine group and/or the guanidine group

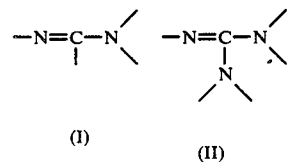

(I)   (II)

one or more times and which contain two, one or no hydrogen atoms reactive to isocyanates at room temperature.

The acylic, monocyclic or bicyclic amidine or guanidine compounds are also referred to hereinafter as "amidine-compounds" or "compounds containing amidine residues" or, quite simply, as "amidine" stabilizers.

The useful amidines are acylic or cyclic amidines, preferably those corresponding to formulae (III) and (VII) below:

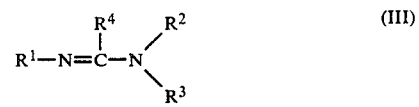

(III)

in which $R^1$ and $R^4$ may be the same or different and represent H, a straight-chain or branched aliphatic hydrocarbon radical containing from 1 to 18 C-atoms (preferably from 1 to 4 C-atoms), a cycloaliphatic hydrocarbon radical containing from 5 to 7 ring C-atoms, an araliphatic radical or an aromatic radical, preferably with 6–13 carbon atoms, which radicals may contain substituents inert under the reaction conditions and/or are interrupted by the structural units —O—, —S—,

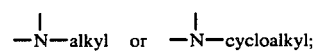

(alkyl and cycloalkyl as defined above); $R^2$ and $R^3$ may be the same as or different from $R^1$ or represent alkylene-N-(di-cycloalkyl) or alkylene-N-(dialkyl) radicals (alkyl- and cycloalkyl as defined above), [preferably —(CH$_2$)$_n$—N—(C$_1$–C$_6$—alkyl)$_2$—radicals n=2–12], but not H. The amidines are preferably mono- or bicyclic amidines in which two of the radicals $R^1$ to $R^4$ are attached to one another to form a ring. Alternatively, several amidine radicals may be attached by polyfunctional radicals. It is noted that when $R^1$ is hydrogen, that hydrogen will not normally react with an isocyanate group at room temperature.

Preferred cyclic amidines include those corresponding to formulae (IV)

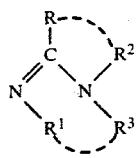
(IV)

where the radicals $R^1$ and $R^3$ together and/or the radicals $R^2$ and $R^4$ together represent a straight-chain or branched alkylene radical with 2 to 5 C-atoms in the alkyl chain and optionally containing heteroatom (group)s such as —O—, —S— or —N—$C_1$-$C_4$—alkyl groups. Preferably, the radicals represent —$(CH_2)_2$— or —$(CH_2)_3$—.

Also preferred are cyclic amidines of the formula V:

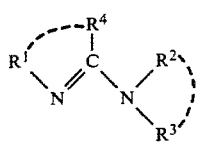
(V)

where $R^1$ and $R^4$ and/or $R^2$ and $R^3$ together represent an optionally branched alkylene radical with 2 to 5 C-atoms in the alkylene chain and optionally contain heteroatoms. Preferably the radicals represent —$(CH_2)_2$— and —$(CH_2)_3$—.

Also preferred are cyclic amidines corresponding to formula (VI):

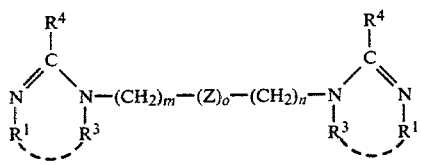
(VI)

in which $R^1$ and $R^3$ are as defined for formula IV; $R^4$ is as defined for formula III, Z is an >N—$C_1$-$C_{18}$—alkyl group or a straight-chain or branched-chain $C_2$-$C_{14}$-alkylene radical which may optionally be interrupted in the chain by —O—, a cycloalkane radical containing from 5 to 8 ring members or a dicyclohexyl-($C_1$-$C_4$-alkane)-radical; m and n may be the same or different and represent integers of from 2 to 10, preferably 2 or 3 and o=zero or 1.

Other particularly preferred amidines are those corresponding to the following formula

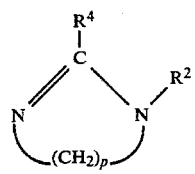
(VII)

in which p=2, 3 or 4, $R^4$ represents a straight-chain or branched $C_1$-$C_4$—alkyl radical (for example methyl, ethyl, isopropyl or tert.-butyl) and, $R^2$ represents a straight-chain or branched $C_1$-$C_4$—alkyl, —$(CH_2)_p$—N—$(R^4)_2$ or $C_5$-$C_7$—cycloalkyl radical.

The following are specific examples of acyclic amidines corresponding to formula (III): N,N-dimethyl formamidine, N,N-dimethyl acetamidine, N,N-diethyl formamidine, N,N,N'-trimethyl acetamidine, N,N-dimethyl-N'-benzyl acetamidine, N,N-dicyclohexyl-N'-methyl acetamidine, N,N-dimethyl-N'-cyclohexyl formamidine, N,N-dimethyl-N'-tert.-butyl formamidine.

The following are specific examples of the particularly preferred monocyclic amidines corresponding to formula (IV): 1,2-dimethyl-Δ2-imidazoline, 1-methyl-2-phenyl-Δ2-imidazoline, 1(N)-methyl-Δ2-imidazoline, 2-benzylimino-N-methyl caprolactam, 2-butylimino-N-methylbutyro-lactam, 1,8-diazabicyclo[5,3,0]-dec-7-ene, 1,8-diazabicyclo[5,4,0]-undec-7-ene, 1,7-diazabicyclo[4,4,0]-dec-6-ene, 1,6-diazabicyclo[3,4,0]-non-5-ene, 1,5-diazabicyclo[4,3,0]-non-5-ene, 1,14-diazabicyclo[11,4,0]-hepta-dec-13-ene, 1-(N)-methyl-Δ2-tetrahydropyrimidine, 1-cyclohexyl-2-methyl-Δ2-tetrahydropyrimidine, 1-cyclohexyl-Δ2-tetrahydropyrimidine, 1-benzyl-2-butyl-Δ2-tetrahydropyrimidine, 1-methyl-2-methyl-Δ2-tetrahydropyrimidine, 1-butyl-2-methyl-Δ2-tetrahydropyrimidine, 1-(2-ethylhexyl)-2-methyl-Δ2-tetrahydropyrimidine, 1-dodecyl-2-methyl-Δ2-tetrahydropyrimidine, 1-(1-methylcyclohexyl)-2-methyl-Δ2-tetrahydropyrimidine, 1-(2-methylhexyl)-2-methyl-Δ2-tetrahydropyrimidine, 1-(3,3,5-trimethylcyclohexyl)-2-methyl-Δ2-tetrahydropyrimidine.

Compounds such as these may be synthesized in particular in accordance with German Auslegeschrift No. 2,439,550.

Especially preferred amidines are those corresponding to the following formula

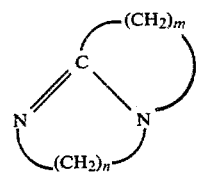
(IVa)

in which m=2, 3, 4, 5 or 11 and n=2, 3, or 4.

The production of a number of such compounds is described, for example, in German Pat. No. 1,545,855.

Examples of compounds corresponding to formula IV containing a lateral dialkylaminoalkyl group $R^2$ include 1-(3-N,N-dimethylaminopropyl)-2-methyl-Δ2-tetrahydropyrimidine and, 1-(2-N,N-dimethylaminoethyl)-2-methyl-Δ2-tetrahydropyrimidine, being produced in accordance with German Auslegeschrift No. 3,049,131.

Examples of the amidines corresponding to formula (V) include 1-methyl-4-(2-tetrahydroazepinyl)-piperazine

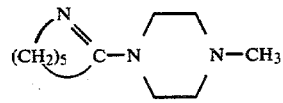

phenyl-methyl-(2-tetrahydroazepinyl)-amine

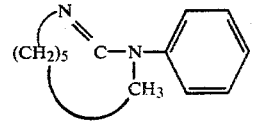

benzyl-methyl-(2-tetrahydroazepinyl)-amine

-continued

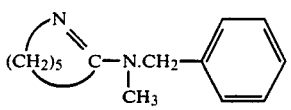

and 4-(2-tetrahydroazepinyl)-morpholine

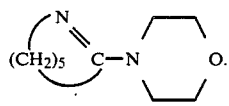

The acyclic amidines or the cyclic or bicyclic amidines formed by the attachment of two radicals are described in German Auslegeschrift No. 2,722,514.

General information on the synthesis of amidines can be found in Houben-Weyl, Methoden der Organischen Chemie, Vol. IX, 2, Pages 38 to 66; Verlag, G. Thiem, Stuttgart 1958.

Compounds corresponding to formula (VI) include, for example

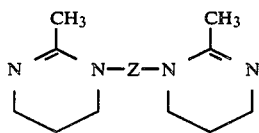

in which Z represents —(CH$_2$)$_2$—, —(CH$_2$)$_6$—,

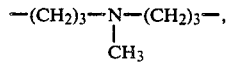

—(CH$_2$)$_6$—NH—CO—O—(CH$_2$)$_3$—O—(CH$_2$)$_3$—O—CO—NH(CH$_2$)$_6$— or —(CH$_2$)$_2$—O—(CH$_2$)$_2$—.

These compounds are obtained by the methods described in German Auslegeschrift No. 3,049,131.

Guanidines used in accordance with the invention preferably correspond to formula (VIII) and include acyclic or cyclic guanidines, but also di- and triguanides and compounds which may repeatedly contain the guanidine radical. The preferred guanidines correspond to formula VIII:

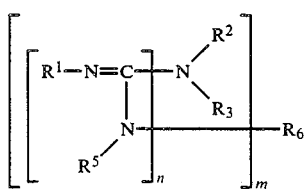

(VIII)

wherein m=1 or 2, n=1, 2, or 3 when m=1, preferably n=1; and n=1 when m=2; $R^1$, $R^2$ and $R^3$ represent radicals of the type defined in reference to the amidines corresponding to formula (III), $R^5$ has the same meaning as $R^2$, $R^6$ represents either a monofunctional radical of the type mentioned for $R^2$ or a difunctional $C_2$-$C_{12}$-alkylene radical which may optionally be interrupted by —O—, —N($C_1$-$C_4$-alkyl)- or —N($C_5$-$C_7$-cycloalkyl)-radicals. When n=1, any group of two of the radicals $R^1$, $R^2$, $R^3$, $R^5$ and $R^6$ may be attached to one another to form a ring. Preferred cyclic guanidines correspond to the following formulae:

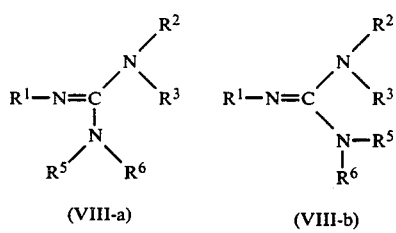

(VIII-a)   (VIII-b)

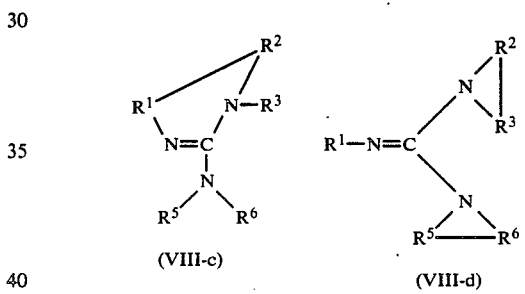

(VIII-c)   (VIII-d)

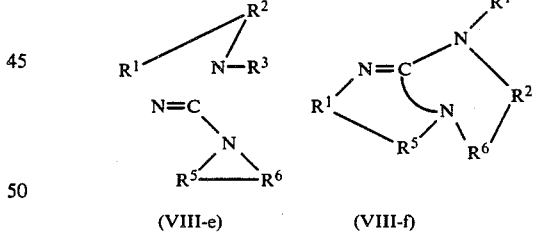

(VIII-e)   (VIII-f)

In formulae (VIII-a) to (VIII-f), the groups formed by the attachment of two of the R's to form the rings preferably are alkylene groups of from 2 to 5 carbon atoms and may optionally be interrupted by heteroatoms (—O—, —S—, —N(alkyl)—) or substituted by substituents inert during the reaction (for example halogen, alkyl).

Other suitable guanidines are shown in the following schedule. It is pointed out that the guanidines in which $R^1$ is hydrogen noramlly do not react with isocyanates at room temperature on that (HN—) group.

| Substituents on the nitrogen | Substituted x-times | in the following primary guanidine structures |
|---|---|---|
| methyl-, ethyl-, (iso)propyl-, (iso)butyl-, (tert.)-butyl-, (iso)pentyl-, hexyl-, 2-ethylhexyl-, octyl-, dodecyl-, stearyl-, ethoxypropyl-, butoxyhexyl-, cyanoethyl-, cyanohexyl-, butoxycarbonyl-methyl-, methoxycarbonylmethyl-, dimethylaminopropyl-, cyclopentyl-, cyclohexyl-, (chloro)benzyl-, phenethyl-, phenyl-, tolyl-, methoxyphenyl-, ethoxycarbonylphenyl-, | tetra penta tri- tri- tri- (CH₂)₅ mono- mono- mono- | (structures shown) |

Further examples are iminocarbonic-acid-bis-(sec.)-amides having the following composition:

| | | |
|---|---|---|
| methylimino- ethylimino- cyanoethylimino- dibutylaminobutylimino- hexylimino- stearylimino- cyclohexylimino- benzylimino- phenylimino- p-chlorobenzylimino- 4-methyl-benzylimino- | carbonic acid | -bis-morpholide -bis-piperidide -bis-N'—methyl-piperazide |

Particularly preferred are tetramethyl guanidine, pentamethyl guanidine and cyclic guanidine compounds of the following formula:

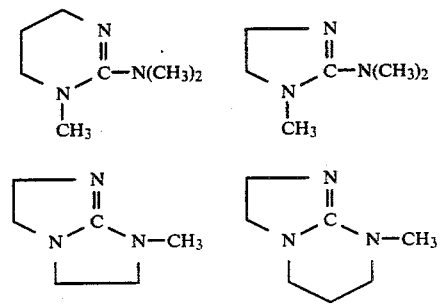

Instead of using the free amidine/guanidine compounds, it is also possible, although less preferred, to use acid addition salts of the amidines or guanidines.

The expression "acid addition salts" is intended to include salts formed with acids and also salts formed with other proton donor compounds. Typical acids for producing these salts include mono-carboxylic acids, such as formic acid, acetic acid, propionic acid, butyric acid, caproic acid, valeric acid, octylic acid, lauric acid, stearic acid, oleic acid; dicarboxylic acids, such as oxalic acid, malonic acid, succinic acid, fumaric acid, adipic acid; hydroxylic acids, such as glycolic acid, lactic acid, tartaric acid and the like; sulfonic acids, such as alkyl or aryl sulfonic acids, sulfamic acid, sulfanilic acid; inorganic acids, such as carbonic acid, phosphoric acid, hydrochloric acid, sulfuric acid and the like and other proton donor compounds, such as sulfonamides; phenols, such as phenol, cresol or thiophenols; enols, such as barbituric acid, uric acid and the like. Fatty acids containing at least two carbon atoms and phenols are particularly preferred.

Where acyclic, mono- or bicyclic amidines or guanidines are used for deactivating the solid polyisocyanates in accordance with the invention, an increase—in some cases a considerable increase—in the surface stabilizing effect is observed when small quantities of water, low molecular weight glycols or amines are added to the reaction mixture.

One feature of the invention in regard to the surface modification of solid polyisocyanates in accordance with the invention is that, the amidines or guanidines used for deactivation stabilize the isocyanates to a considerable extent at room temperature, even with respect to aromatically or aliphatically bound $NH_2$-groups (for example in relatively high molecular weight aliphatic polyamines) and then fully develop their catalytic activity above the thickening temperature during the thermal crosslinking step. Thus, there is generally no need for other catalysts of the type which would be required for the rapid solidification of sluggishly reacting H-active compounds (for example with secondary OH terminal groups or even with water).

It can be of advantage to use amidines and guanidines in particular when, in addition to the above-mentioned stabilization of the polyisocyanates, it is intended to catalyze the high-temperatures NCO-reaction with the H-active groups of the substrate. In addition, amidines and guanidines can initiate further NCO reactions at elevated temperature, such as for example cleavage of the uret dione ring in the case of dimeric polyisocyanates and trimerization, allophanatization or biuretization in the case of the polyisocyanates mentioned. These further reactions can produce a significant improvement in adhesion.

It is of course possible to use any combinations of the stabilizers mentioned, for example to offset adverse side effects of an amine or amidine by corresponding advantages of other amines or amidines (for example low molecular weight and relatively high molecular weight diamines used together) or to combine as many favorable side effects as possible. Thus, suitable combinations are, for example, combinations of fast-reacting amines, such as ethylene diamine, with amines retarded by stearic hindrance and combinations low molecular weight amines with high molecular weight amines, such as aliphatic aminopolyethers, or of polyamines with hydrazines or hydrazide derivatives. For example, up to 50 mole percent of polyamines, based on the total quantity of "stabilizers" used, can be used in addition to hydrazine or hydrazide derivatives or amidines or guanidines.

Combinations of amines and amidines are also of advantage when it is intended to balance the stabilizing effect (influence on the processing temperature and time) with the amidine-promoted further NCO reactions on the other hand. The compounds (D) are used in quantities of 50-100 equivalent % per NCO-equivalent in (B). In the case of hydrazine, an $NH_2$—equivalent is an $NH_2$—group (or an —NH— alkyl group in the case of alkyl hydrazine derivatives) whereas, in the case of "hydrazide" compounds, a —$CO.NH.NH_2$—group counts as an $NH_2$-equivalent.

The coating reactions are carried out at temperatures below the particular melting temperatures of the polyisocyanate (A) or of the "covered polyisocyanates (A) and (B)". They are generally below 70° C. and preferably in the range from 0° to 50° C.

Stabilization of the isocyanate is generally completed within a few minutes which allows for continuous working of the stabilizing reaction which may optionally be selected in regard to the type and quantity of component (C) (for example polyols) used for stabilization in such a way that its composition directly corresponds to the thermally hardenable reactive PU mixture.

The "stabilization" of the solid polyisocyanates by coating with polyadduct is carried out in component (C) which is either not a solvent for the solid polyisocyanates (A), or, more particularly, not a good solvent for the polyisocyanates (B) used for covering. The component (C) serves to liquidize, suspend or partially dissolve component (B) in the case where (B) is solid (not preferred). In any case (C) must not prevent absorption or deposition of (B) on (A). The corresponding solvents, plasticizers or polyols have already been mentioned.

Component (C) may consist with advantage of relatively high molecular weight polyols having molecular weights of from 400 to 6000. However, it is preferred to use relatively high molecular weight polyols having molecular weights in the range from 400 to 3000 and particularly preferred to use relatively high molecular weight polyols having molecular weights in the range from 1000 to 3000, optionally in combination with low molecular weight polyols and/or aromatic low molecular weight polyamines. In the polyols, the particles of (A) can be suspended or the polyisocyanate (B) can be easily dispersed.

Component (C) may also consist of plasticizer-like compounds, for example adipates or phthalates such as dioctyl, diisododecyl, dibenzyl, butylbenzyl phthalate. Hydrocarbons, such as so-called butadiene oils, or polyethers of relatively high molecular weight may also be used. In that case, the procedure generally adopted is for the finely powdered, solid isocyanate (A) to be covered with the other polyisocyanate (B) and stirred with a solution of the stabilizer in the plasticizer at a temperature around ambient temperature. If it is desired to use the stabilized isocyanates in this suspension, the other starting components required, such as relatively high molecular weight aromatic polyamines for example, may be added after stabilization of the polyisocyanate by coating with polymer.

It is also possible, although not preferred, to isolate the stabilized, foreign-polymer-coated polyisocyanates, for example by filtration or evaporation of the solvent, and then to suspend them in a relatively high molecular weight polyol and polyamine compounds.

The polymer-coated polyisocyanates may be directly produced in suspension in, preferably, relatively high molecular weight polyols (optionally in conjunction with low molecular weight polyols or aromatic polyamines as chain-extending agents), but preferably in relatively high molecular weight polyamines containing aromatic amimo groups (optionally in conjunction with low molecular weight aromatic polyamines and/or low molecular weight polyols as chain-extending agents), so that they are present in the form of a suspension which may be directly used as such for one-component reactive polyurethane systems.

This may be done, for example, by adding suspensions of the covered polyisocyanates (A plus B) in hexane or diisopropyl ether while stirring to the polyols or relatively high molecular weight polyamines which contain the polymer-forming stabilizers (D) in solution.

However, in addition to in situ production in the polyols or aromatic polyamino compounds, the stabilized polyisocyanates may also be produced by reacting the covered polyisocyanates with the stabilizers (D) in weakly polar solvents, plasticizers or, optionally, water, and separating off the (foreign)-polymer-coated stabilized polyisocyanates formed, for example by filtration, isolating them and then suspending them in (relatively high molecular weight) polyols and/or polyamines.

The polyisocyanates stabilized in accordance with the invention show extremely high stability in storage in the suspended polyols and/or relatively high molecular weight polyamines, even at elevated temperatures and even in the presence of highly active polyurethane catalysts. Where the coated polyisocyanates according to the invention are used, reactive PU mixtures containing even aromatic diamines as chain extenders show excellent stability in storage or a greatly prolonged pot life in casting systems, even when the polyamines used are soluble, liquid aromatic polyamines.

The long-lasting, free-flowing and, optionally, readily fusible, heterogeneous one-component systems formed with the stabilized polyisocyanate may also be hardened by the addition of polar solvents (for example dimethyl formamide) and, in some cases, simply by the application of powerful shear forces.

For thermal hardening, the one-component reactive polyurethane systems according to the invention may be reacted at temperatures in a relatively low range (above the thickening temperature, preferably at 55° C. and, more preferably, at 100° to 135° C.). Polyurethane plastics of high quality are obtainable.

The relatively high molecular weight polyols include for example, polyoxyalkylene polyols, for example polyoxytetramethylene glycols, or ethoxylation and/or propoxylation products of low molecular weight di- and polyols or di- and polyamines, for example propoxylated trimethylol propane, propoxylated ethylene diamine or linear or branched polypropylene glycol ethers which may contain oxyethylene groups in random, block-like or terminal form and which, overall, have molecular weights of from 400 to 6000.

In one embodiment, for example, difunctional or higher, relatively high molecular weight polyols, optionally in conjunction with low molecular weight polyols, are used as the liquid medium for suspending the stabilized polyisocyanates which are directly used as reactants containing hydroxyl groups in the production of polyurethanes.

Accordingly, it is possible to use any of the relatively high molecular weight compounds containing terminal OH-groups normally used for the synthesis of polyurethanes, such as polyethers, polyacetals, polythioethers or even polyesters; examples of these compounds can be found in German Offenlegungsschrift No. 2,920,501.

Where the suspension of the stabilized polyisocyanates in the polyols is directly used for one-component polyurethane systems, the (relatively high molecular weight) polyols may also contain corresponding quantities of low molecular weight polyols, preferably diols, and/or, more particularly, aromatic polyamines, preferably diamines, as chain-extending agents which have molecular weights of from 62 to 399. In many cases, these chain-extending agents are only added to the suspensions of the polyisocyanates on completion of the coating reaction. The low molecular weight aromatic polyamines may also be added with particular advantage to the system (as chain-extending agents) where corresponding one-component polyurethane systems are being produced. The components are preferably reacted in quantities which correspond to the formulation of the one-component polyurethane systems.

Suitable relatively high molecular weight polyhydroxyl compounds, which may be used both as suspension medium for the polyisocyanates and also as further reactive components for the production of polyurethanes, include difunctional or high polyhydroxyl compounds containing from 2 to 8 and preferably from 2 to 4 hydroxyl groups and having a molecular weight of from 400 to 6000. The polyhydroxyl compounds in question include polyesters, polyethers, polythioethers, polyacetals, polycarbonates, polylactones or polyester amides containing at least two hydroxyl groups and also polybutadiene compounds or mixtures thereof, of the type known for the production of homogeneous, cellular or foam-like polyurethanes. Polyethers and polyesters are particularly preferred.

The polyethers in question are known and are obtained, for example, by polymerizing tetrahydrofuran or epoxides, such as ethylene oxide, propylene oxide, butylene oxide, styrene oxide or epichlorohydrin or by the addition of these epoxide compounds (preferably ethylene oxide or propylene oxide), optionally in admixture or successively, onto starter components containing reactive hydrogen atoms, such as water, polyhydric alcohols, ammonia or polyfunctional amines or sugars.

The hydroxyl-containing polyesters in question include, for example, reaction products of polyhydric, preferably dihydric, and optionally trihydric and higher alcohols with polybasic, preferably dibasic, polycarboxylic acids or their anhydrides or corresponding polycarboxylic acid esters of lower alcohols.

Polyesters of lactones, for example, $\xi$-caprolactone, or of hydroxy carboxylic acids, for example $\omega$-hydroxy caproic acid, may also be used, particularly if they contain additional components, such as diethylene glycol or 1,4-butane diol, to reduce their high crystallinity.

Suitable polyacetals include, for example, the compounds obtainable from glycols and formaldehyde.

The hydroxyl-containing polycarbonates in question include those, for example of the type which may be obtained by reacting 1,3-propane diol, 1,4-butane diol and/or 1,6-hexane diol, di-, tri- or tetraethylene glycol or thiodiglycol, with diaryl carbonates, (for example, diphenyl carbonates) or phosgene.

Polybutadienes containing terminal hydroxyl groups are also suitable for use in accordance with the invention because they give particularly elastic and hydrolysis-stable products. It is also possible to use polyhydroxyl compounds containing high molecular weight polyadducts for polycondensates or polymers in finely dispersed or even dissolved form. Polyhydroxyl compounds such as these are obtained, for example, by carrying out polyaddition reactions, (for example reactions between polyisocyanates and amino functional compounds) or polycondensation reactions (for example between formaldehyde and phenols and/or amines) in situ in the above-mentioned compounds containing hydroxyl groups.

Polyhydroxyl compounds modified by vinyl polymers, of the type obtained, for example, by polymerizing styrene and acrylonitrile in the presence of polyethers or polycarbonate polyols, are also suitable for use in the process according to the invention.

Further representatives of the above-mentioned compounds suitable for use in accordance with the invention are described in detail, for example, in High Polymers, Vol. XVI, "Polyurethanes, Chemistry and Technology", by Saunders-Frisch, Interscience Publishers, New York/London, Vol. I, 1962, Pages 32 to 42 and Pages 44 to 54 and Vol. II, 1964, Pages 5 to 6 and 198 to 199, and in Kunststoff-Handbuch, Vol. VII, Vieweg-Hochtlen, Carl-Hanser-Verlag, Munich, 1966, for example on Pages 45 to 71 and in DE-A No. 2,854,384.

It is of course possible to use mixtures of the above-mentioned polyhydroxyl compounds. The polyhydroxyl compounds may of course also be pre-extended with substoichiometric quantities of diisocyanates.

Liquid or low-melting (<50° C.), low molecular weight and/or relatively high molecular weight aromatic polyamines and/or relatively high molecular weight aliphatic polyamines can also be used for the production of one-component reactive PU systems.

The relatively high molecular weight polyamino compounds containing aromatic amino groups and having molecular weights in the range from 400 to 6000 which are used in accordance with the invention include, in particular, polyamino compounds of the type which can be obtained by the (preferably basic) hydrolysis of the corresponding isocyanate-terminated prepolymer based on relatively high molecular weight polyhydroxyl compounds and excess aromatic diisocyanates. Examples of this process are given in German Auslegeschriften Nos. 2,948,419, 3,039,600, and 3,112,118 and European Patent Application Nos. 61,627, 71,132, 71,139 and 97,869. The first of these patents also mentions other state-of-the-art processes for producing aromatic amino compounds of relatively high molecular weight structure of the type suitable for use in the process according to the invention. The process according to German Auslegeschrift No. 2,948,419 and the other patents cited are preferably used for the production of polyether polyamines, although they may also be used for the production of polyester, polyacetal, polythioether or polycaprolactone polyamines, and preferably di- or trifunctional polyamines which contain urethane groups (from the reaction of the corresponding relatively high molecular weight polyhydroxyl compounds with the excess polyisocyanate) and which carry the amino groups on the residue of the (former) polyisocyanate. However, the aromatic, relatively high molecular weight polyamines may also be produced by other methods, for example, by reacting NCO-prepolymers with excess quantities of hydrazine, amino phenylethylamine or other diamines in accordance with German Auslegeschrift No. 1,694,152. Another possible method is described in French Pat. No. 1,415,317, according to which the NCO-prepolymers are converted by reaction with formic acid into the N-formyl derivatives which are then hydrolyzed. The reaction of NCO-prepolymers with sulfamic acid in accordance with German Auslegeschrift No. 1,155,907 also gives polyamines of relatively high molecular weight.

In addition to amino groups (from aromatic polyisocyanates) attached to aromatic radicals, it is also possible to produce, by using aliphatic polyisocyanates, relatively high molecular weight polyamine compounds containing amino groups attached to aliphatic radicals.

These relatively high molecular weight aliphatic polyamines, of the type already described as relatively high molecular weight stabilizers, may be used both as stabilizer and also as the relatively high molecular weight polyamino compound where the stabilizing reaction is carried out at low temperatures, for example room temperature. However, if the temperature is correspondingly increased, for example to 120° C., all the aliphatic amino groups are fully reacted with the isocyanate groups. In this case, elastomers may be directly obtained providing the ratio between NCO-groups and NCO-reactive groups (OH— and/or NH$_2$—groups) is exactly in the polymer-forming range.

Apolar or weakly polar solvents, for example aliphatic, cycloaliphatic or aromatic hydrocarbons, halogenated hydrocarbons, ethers, ketones or esters, preferably having boiling points below 146° C., are sometimes added to the liquid media mentioned above (polyols, polyamines, plasticizers or water). as to obtain a reaction in a medium of lower viscosity. The solvents are best removed again afterwards, for example by distillation in vacuo.

The stabilizing reactions described in the foregoing produce a suspension of polymer-coated, stabilized polyisocyanates in the liquid medium (i.e. component (C)).

The suspensions contain at least 3% by weight, preferably at least 5% by weight and, in most cases, at least 7.5% by weight of solid, stabilized polyisocyanates. The solids contents are generally below 70% by weight, preferably below 50% by weight and, in most cases, below 40% by weight.

If the polyisocyanates are suspended in a medium, (for example relatively high molecular weight polyols or polyamines) which is suitable for the further polyurethane-forming reactions, this suspension may be directly used as such. However, it is possible, although less preferred, to isolate the stabilized polyisocyanates from the suspension, for example by filtration, especially where water or a large quantity of plasticizer and/or solvent is used and to add it in powder form to the desired reaction components (the relatively high molecular weight polyols and/or polyamines, optionally other relatively high molecular weight polyols of identical or different structure and, optionally, low molecular weight chain extending agents. Low boiling components (C) (e.g. solvents) can be distilled from the suspension. Such distillate is preferably done in vacuo.

Particular significance is attributed in practice to storable suspensions of the stabilized polyisocyanates in relatively high molecular weight polyamines, optionally in combination with other relatively high molecular weight polyols and/or chain-extending agents (for example low molecular weight polyamines and low molecular weight polyols) of the type which may be directly used for one-component reaction and for the formulation of one-component systems. The components are preferably reacted in quantitative and equivalent ratios which directly correspond to a formulation of one-component reactive PU systems.

The one-component reactive systems according to the invention are preferably produced using low molecular weight chain-extending agents or cross-linking agents. These low molecular weight chain-extending agents or crosslinking agents are compounds having a functionality of two or more which contain hydroxyl groups attached to aliphatic and/or cycloaliphatic groups (polyols) and/or $NH_2$—groups attached to aromatic—including heterocyclic—rings (polyamines) and which have molecular weights of from 62 to 399. Low molecular weight diols containing hydroxyl groups attached to aliphatic or cycloaliphatic groups and aromatic diamines having a molecular weight of up to 399, as indicated above, are preferred. These compounds generally contain from 2 to 8, preferably from 2 to 4 and, more preferably 2 isocyanate-reactive hydrogen atoms such as hydroxyl and/or amino groups. Mixtures of different compounds of this type may of course also be used. Examples of such compounds include ethylene glycol; trimethylene glycol; 2,3- and/or 1,4-butane diol; 1,6-hexane diol; neopentyl glycol; 1,4-bis-hydroxyethyl cyclohexane; 1,4-dihydroxy cyclohexane; terephthalic acid-bis-($\beta$-hydroxy-ethyl)-ester; 1,4,3,6-dianhydrohexitols; 1,4-mono-anhydrotetritols; and, less preferably, diols containing secondary hydroxyl groups, such as, for example, propylene glycol, 2,3-butane diol or 2,5-pentane diol. Examples of polyfunctional compounds include trimethylol propane; trimethylol ethane; 1,2,6-hexane triol; glycerol; pentaerythritol; quinitol; mannitol; sorbitol; castor oil; di-, tri- and tetra-ethylene, propylene and butylene glycols; bis-(2-hydroxyethyl)-hydroquinone; bis-(2-hydroxyethyl)-resorcinol; formose; or formitol. Diols or polyols containing tertiary amines, such as N-methyl diethanolamine, triethanolamine or N,N'-bis-hydroxy-ethyl piperazine, are also suitable.

Low molecular weight aromatic diamines are preferably used instead of low molecular weight polyols. Aromatic polyamines are also understood to include amines in which the amino group is attached to heterocyclic radicals of aromatic character. Examples of suitable aromatic polyamines include, for example, p-phenylene diamine; 2,4-/2,6-tolylene diamines; diphenylmethane-4,4'- and/or -2,4'- and/or -2,2'-diamines; 3,3'-dichloro-4,4'-diaminodiphenylmethane; 3-($C_1$–$C_8$)-alkyl-4,4'-diaminodiphenylmethanes; 3,3'-di-($C_1$–$C_4$)-4,4'-diaminodiphenylmethanes; 3,3',5,5'-tetra-($C_1$–$C_4$)-alkyl-4,4'-diphenylmethanes; 4,4'-diaminodiphenyl sulfides, sulfoxides or sulfones; diamines containing ether groups according to German Auslegeschriften No. 1,770,525 and 1,809,172 (U.S. Pat. Nos. 3,654,364 and 3,736,295); 2-halogen-1,3-phenylene diamines optionally substituted in the 5position (German Auslegeschriften Nos. 2,001,772, 2,025,896 and 2,065,869); bis-anthranilic acid esters (German Auslegeschriften Nos. 2,040,644 and 2,160,590); 2,4-diaminobenzoic acid esters according to German Auslegeschrift Nos. 2,025,900; and tolylene diamines substituted by one or two ($C_1$–$C_4$)-alkyl groups. Particulary preferred are 3,5-diethyl-2,4- and/or -2,6-diaminotoluene particularly their technical (80:20)- or (65:35)-isomer mixtures); asymmetrically tetra-alkyl-substituted diaminodiphenylmethanes, for example 3,5-diethyl-3',5'-diisopropyl-4,4'-diamino-diphenylmethane and isomer mixtures thereof according to German Auslegeschrift No. 2,902,090, 4,4'-diaminobenzanilide; 3,5-diaminobenzoic acid-($C_1$–$C_4$)-alkyl esters; 4,4'-and/or 2,4'-diaminodiphenylmethane; and naphthylene-1,5-diamine.

The aromatic diamines are preferred to the glycols. However, it is also possible to use diols or diamines containing additional groups, for example adipic acid-bis-(2-hydroxyethyl)-ester; terephthalic acid-bis-(2-hydroxyethyl)-ester; diol urethanes; diol ureas; or polyols containing sulfonate and/or phosphonate groups. Specific examples include 1,6-hexamethylene-bis-(2-hydroxyethyl-urethane), 4,4'-diphenylmethane-bis-(2-hydroxyethylurea) or the adduct of sodium bisulfite with 1,4-butene diol and alkoxylation products thereof. Other low molecular weight compounds are described in detail in German Auslegeschrift No. 2,854,384.

In addition, isocyanate-monofunctional compounds may optionally be used in the usual way as so-called chain terminators in quantities of from 0.01 to 10% by weight. Monofunctional compounds of this type are, for example, monoamines, such as butyl or dibutylamine, stearylamine, pyrrolidine, aniline or tolylamine, butanol, 2-ethylhexanol, cyclohexanol or ethylene glycol monoethyl ester.

The catalysts used for the long-lasting one-component systems according to the invention may be the usual polyurethane catalysts, although organic lead and/or tin compounds may be used with particularly good effect, optionally in combination with other standard polyurethane catalysts, particularly catalysts containing tertiary amines.

Among the lead compounds, compounds from the following group are preferred:
(a) organic salts of divalent lead with carboxylic acids.
(b) dithiocarbamates of divalent lead.

Suitable organotin compounds are tin-(II) salts of carboxylic acids, such as tin acetate, tin octoate, tin-(III) ethylhexanoate and tin laurate; and tin-(IV) compounds, for example, dibutyl tin oxide, dibutyl tin dichloride, dibutyl tin diacetate, dibutyl tin dilaurate or dibutyl tin maleate.

Preferred tin catalysts are sulfur-containing tin compounds such as, for example, di-(octyl)-tin-(IV)-bis-thiomethyl or dimethyl tin-(IV)-bis-thiolauryl, and dimethyl tin bis-thioglycolic acid hexyl ester or dibutyl tin bis-thioglycolic acid octyl ester.

Also useful are combinations of the organometallic compounds with aminopyridines, hydrazinopyridines (German Auslegeschriften Nos. 2,434,185, 2,601,082 and 2,603,834) or 1,4-diazabicyclo-2,2,2-octane and/or standard tert.-amine catalysts of the type normally used in polyurethane chemistry.

The lead catalysts are particularly effective when polyether polyols containing secondary hydroxyl groups, for example polypropylene glycols, are used in the system. Where uret dione diisocyanates are used, additional crosslinking can occur through cleavage of the uret dione ring, particularly where lead catalysts are used, although in that case branching allophanate groups or, in the event of complete cleavage of the uret dione ring, additional urethane groups are formed.

By contrast, where polyols essentially containing primary hydroxyl groups are used, the tin compounds, particularly the tin/sulfur catalysts, are particularly effective. In the case of polyethers containing aromatic NH$_2$-groups, there is generally no need at all for catalysis. The catalysts, when used, are used in a quantity of from 0.001 to 5% by weight and preferably in a quantity of from 0.01 to 2% by weight, based on (A)+(B).

Auxiliaries and additives may optionally be used and include dyes or pigments; fillers, such as silica gel, gypsum, talcum, active carbon and metal powders; UV-absorbers or stabilizers, such as phenolic antioxidants; light stabilizers; blowing agents, such as $CO_2$ or fluorodichloroalkanes; surface-active additives, such as emulsifiers or foam stabilizers; cell regulators; antiblocking agents; silicones; flame-proofing agents or fungistatic and/or bacteriostatic substances.

Suitable fillers include, for example, fibrous materials, i.e. any inorganic and/or organic fibrous reinforcing materials know per se.

The quantity of filler to be incorporated depends upon the required improvement in the mechanical properties and generally amounts to between 5 and 60% by weight of fibrous material.

The NCO:(NH$_2$+OH) ratio (NCO from polymerstabilized polyisocyanate (E) and optionally other, free polyisocyanate to amino and/or OH-groups from relatively high molecular weight polyols and/or polyamines and/or chain-extending agents) in the polyurethane-forming reaction amounts to between 0.5:1 and 1.5:1, preferably to between 0.8:1 and 1.5:1 and, more preferably, to between 0.95:1 and 1.2:1 (equivalents).

From 0.3 to 10, preferably from 0.5 to 8 and, more preferably, from 0.75 to 5 equivalents of (OH+NH$_2$)-equivalents of chain-extending agents, i.e. low molecular weight polyols or low molecular weight polyamines, per (OH+NH$_2$)-equivalent of relatively high molecular weight polyols and/or polyamines are optionally used in the reactive polyurethane mixtures.

(Dimeric) diisocyanates containing uret dione rings may generally be regarded as diisocyanates so that only the free NCO-groups are taken into consideration. Under certain test conditions (presence of lead catalysts, or relatively high processing temperature, for example >140° C.), however, the uret dione ring enters into the reaction (additional points of attachment via allophanate or biuret groups), so that the latent NCO-groups of the uret dione ring have to be taken into account in the calculation.

The one-component reactive PU mixture obtained may readily be applied by casting or knife coating at room temperature or may even be solid at room temperature and readily fusible, depending upon the viscosity and melting behavior of the starting components. These reactive mixtures are a heterogeneous suspension of the solid, stabilized isocyanates in the polyol and/or polyamine components. The thermal crosslinking of this mixture is generally carried out after the addition of suitable catalysts. In the absence of these catalysts, the polyurethane moldings may have unsatisfactory properties, particularly where polyols are used as the relatively high molecular weight compounds or chain-extending agents. However, there is no need to add catalysts in cases where the aromatic polyamine compounds distinctly more reactive to NCO-groups are used on their own.

Another feature of the one-component PU-reactive systems is that they crosslink in a few minutes after reaching a certain temperature (dependent upon the type and quantity of stabilizer amine used). This means on the one hand that, below that temperature ("thickening temperature"), the desirable, long flow of the as yet uncrosslinked reactive mixture enables the hot mold to be completely filled, while on the other hand, the following, rapid solidification of the casting mixtures after an increase in temperature provides for rapid mold release cycles. Another advantage of the invention is the very long shelf life of the starting reactive systems, even at relatively high storage temperatures (for example up to 60° C). In this connection, the advantage over the prior art, where a retarded reaction in one-component systems is only achieved through the "heterogeneity" of one or more components, is additionally improved to a considerable extent through protection by a polyadduct coating, the "protection" only being removable by the heat shock (or by very powerful shear forces or dissolution by highly polar solvents). Use of polyisocyanate suspensions according to the invention greatly broadens the potential applications of one-component systems. It is possible to use liquid and not just solidifying polyamine and polyol systems of relatively high molecular weight and also a range of, and not just selected, chain-extending agents (for example high-melting chain-extending agents). An important feature of the one-component systems according to the invention is that aromatic diamines, such as for example 4,4'-diaminodiphenylmethane, 2,4- or 2,6-diaminotoluene, 3,5-diethyl-2,4:-2,6-(65:35)-diaminotoluene, 1,5-diaminonaphthalene or 3,5-diethyl-3',5'-diisopropyl-4,4'-diaminodiphenylmethane, may also be used as chain-extending agents in these systems without losing the character of a one-component system. If, by contrast, these diamines are reacted with NCO-prepolymers in one of the hitherto standard processes, extremely short casting times are obtained, preventing the mixtures from levelling satisfactorily in the mold.

By using relatively high molecular weight polyamines in the one-component system, it is possible to obtain polyurethane (urea)s having distinctly more favorable properties (for example greater strength, higher moduli, greater hardness and higher softening ranges) than with relatively high molecular weight polyols in the reactive PU mixture alone.

The optionally catalyst-containing one-component systems according to the invention are solidified essentially by heat shock. At room temperature or moderately elevated temperature, there is surprisingly no crosslinking reaction, even in the presence of these powerful catalysts, so that even catalysts-containing mixtures count as long-lasting one-component systems.

The processing of the one-component systems according to the invention depends upon their state. Liquid systems pourable at room temperature may be processed by casting. They may have to be briefly heated before processing, for example to 50°–70° C. They may also be processed by centrifugal casting. Hollow bodies may be produced by introducing the reactive mixture into heated molds and distributing it over the surface of the molds by appropriate rotational movements.

Processing may also be carried out by slush molding. In that case, heated molds may be filled with the reaction mixture and, after a certain period of reaction on the heated mold surface, excess, unreacted reaction mixture is poured out of the molds again.

Where blowing agents are used, it is possible to produce cellular polyurethanes optionally having an integral skin structure.

Systems which cannot be poured, but which level, may be applied, for example by knife-coating, to any desired substrates, for example, textile substrates including nonwovens, knitted fabrics and woven fabrics; leather (skiver); matrices (for example velour leather/silicone matrices); or intermediate supports (for example release papers), to form coatings or finishes which are subsequently hardened by heating.

Plastic systems or pastes may be molded under heat and pressure, for periods of only 5 to 15 minutes at 120° C. being sufficient for hardening.

Surface coatings, impression molds or moldings may even be produced by the immersion process in which the heated molds to be coated are dipped into the reactive mixture.

The reactive mixture may also be extruded through slots or nozzles into hot media (hot air or hot liquids) are hardened in that way.

The reactive mixtures may be completely or largely reacted in heated extruders to form the polyurethane, extruded in that form through slots or nozzles and, optionally, reacted to completion in hot media. Alternatively, it may be introduced into hot molds and removed therefrom after a short time. The reactive mixture may also be processed by reaction injection molding (RIM).

Solid systems, particularly those based on relatively high melting starting polyols (45° to 65° C.), are processed either under pressure in molds (injection molding) or at or above the melting temperature of the polyol. To this end, the previously prepared one-component systems are introduced in the form of solid granulates into a mold heated to beyond the melting point of the polyol (generally below 70° C.). After the granulates have melted and filled the mold, the mold is heated to 100°–120° C. and its contents solidified.

The solidification temperature of the one-component systems according to the invention depends to a large extent upon the quantity and chemical constitution of the components used for stabilizing the polyisocyanates (A). The solidification time required for forming the polyurethanes decreases with increasing solidification temperature. The heating time may amount to less than 1 minute or even to several hours, depending on the temperature. In some cases, it is of advantage to temper the plastics for a while at 100° C. after removal from the mold in order to guarantee complete hardening. The reactive polyisocyanate systems according to the invention also make it possible in particular to produce moldings of large volume without change in the thickening temperature of the system.

However, the one-component reactive systems may also be hardened by the addition of preferably highly polar solvents, such as dimethyl formamide, N-methyl pyrrolidone, or moderately polar solvents, such as propylene carbonate, dioxane or glycol monomethyl ether acetate. The stabilizing effect which the polymer coating has upon the polyisocyanates in the one-component systems may be partly or completely eliminated, depending on the quantity in which these solvents are used. The casting time (pot life) of mixtures such as these may be controlled through the quantity of solvent added. With small quantities, the systems obtained have a pot life of several days at room temperature whereas the systems obtained with larger additions solidify after only 10 to 15 minutes or even suddenly. Once again, the quantity of solvent added depends upon the type and quantity of polymers used (quality of the polyadduct skin over the isocyanate surface) and is determined for the particular systems by practical preliminary tests. The technical advantage of reaction mixtures such as these lies in the fact that they solidify in the absence of heat. The thermal solidification time of the one-component systems may of course also be shortened and adequate stability in storage imparted by suitably dosing the solvents.

Solidification of the one-component systems according to the invention may also be brought about by the application of powerful shear forces, for example in high-speed mixers. The heat effect which occurs with brief stirring generally does not reach the crosslinking-thickening temperature of the one-component systems, so that the polyurea skin on the surface of the isocyanate particles is destroyed solely by mechanical stressing during the mixing process.

It is preferred to use reactive PU systems which contain relatively high molecular weight polyamines and/or chain-extending agents (preferably low molecular weight aromatic polyamines) as components and which, accordingly, give high quality elastomers, coatings, cellular elastomers and moldings optionally having a density distribution characterized by a cellular inner core and a more compact outer skin. Determination of the "thickening temperature" (ADT) of one-component reactive systems: Samples of the liquid or paste-like suspensions containing polymer-coated polyisocyanates in the relatively high molecular weight and/or low molecular weight polyols and/or polyamines (as one-component reactive systems) are applied in an approximately 1 cm wide trace to a Kofler bench. The beginning of solidification of the system to form a polyurethane is determined after waiting for 15 minutes and the associated "thickening temperature" is read off. (For relatively reactive systems, of the type used for example for reaction injection molding, the value may be determined after only 5 or 10 minutes.)

The abbreviations used in the description and in the examples have the following meanings:
TDI=2,4-tolylene diisocyanate
TT=finely divided, solid dimer of 2,4-tolylene diisocyanate
N=biuretized hexane-1,6-diisocyanate (approximately 21.3–21.7% of NCO in the solid)
HDI-trim=trimerized hexane-1,6-diisocyanate
HDI=hexane-1,6-diisocyanate
NDI=naphthylene-1,5-diisocyanate
MDI=diphenyl methane-4,4'-diisocyanate
Dim-MDI=dimeric/oligomeric MDI (containing uret dione groups)
TDIH=4,4'-dimethyl-3,3'-diisocyanatodiphenyl urea
IPDI=isophorone diisocyanate
IPDI-trim=trimer of IPDI
DMDAD=3,3'-dimethyl-4,4'-diaminodicyclohexyl methane
DIP=diisopropyl ether.
AAPE=aromatic amino polyether, NH number 48.4, produced in accordance with German Offenlegungsschrift No. 3,039,600 by the alkaline hydrolysis of an NCO-prepolymer of a linear polyoxypropylene diol (molecular weight 2000) and 2,4-tolylene diisocyanate in a molar ratio of 1:2 (NH number 48.4).

The invention is further illustrated but is not intended to be limited by the following examples in which all parts and percentages are by weight unless otherwise specified.

EXAMPLES

Example 1

I. Covering solid di- or polyisocyanates with liquid di- or polyisocyanates

1.1 Covering TT with N
1.1.1. Covering procedure:

A solution of 62.5 g of biuretized 1,6-diisocyanatohexane (N) having an NCO-content of 21.3% by weight in 30 g of toluene is added dropwise with vigorous stirring over a period of 30 minutes at room temperature to a suspension of 250 g of finely divided, solid, dimeric 2,4-diisocyanatotoluene (TT) in 850 g of hexane. After 1 hour, the solid end product is filtered off under suction and dried (yield 312 g). Hardly any more dissolved isocyanate can be detected in the filtrate.

1.1.2 Characterizing the covered polyisocyanate obtained in accordance with 1.1.1:

A free-flowing white powder is obtained, containing the solid dimeric tolylene diisocyanate (TT) in its core and the biuretized polyisocyanate (N) adsorbed at its surface in a proportion of 20% of (TT+N) Comparison Test with 1.1.1 (in toluene as sole solvent).

62.5 g of N in 30 g of toluene are added with stirring to a suspension of 250 g of (TT) in 850 g of toluene. After 1 hour, the solid polyisocyanate is filtered off under suction and washed with a little petroleum ether. Only the quantity of TT used is recovered (effectively 245 g) while the polyisocyanate N is present in the expected concentration in the filtrate, as determined by NCO-titration. Accordingly, there is no effective "covering" of TT with N in toluene as the sole solvent. Toluene is obviously too good a solvent for the polyisocyanate N which is thus not deposited on the TT, but instead remains dissolved in toluene.

1.2 Covering of NDI with N
1.2.1 Covering procedure:

A solution of 5 g of polyisocyanate N in 5 g of toluene is added with vigorous stirring at room temperature to a suspension of 20 g of 1,5-diisocyanatonaphthalene (NDI), NCO-content=39.4%, in 50 g of hexane. After a short time, the solid product is filtered off under suction and dried. A yield of 24.5 g is obtained. Hardly any more NCO can be detected in the filtrate.

1.2.2 Characterization of the polyisocyanate covered in accordance with 1.2.1:

The covered isocyanate is a free-flowing powder having an NCO-content of 35.6% (calculated 35.9% for the NDI/N mixture) and a softening point of 120° to 121° C.

1.3 Covering MDI with IPDI/trim
1.3.1 Covering procedure:

A solution of 7.5 g of a trimer of isophorone diisocyanate in 5 g of toluene is added dropwise to a suspension of 20 g of solid, crystallized 4,4'-diisocyanatodiphenylmethane in 50 g of hexane (cooled to below 10° C. in an ice bath). After stirring for 30 minutes, the solid product is filtered off under suction and dried at 20° C. in a water jet vacuum. The filtrate of the solvents is substantially free from polyisocyanates.

1.3.2 Characterization of the covered polyisocyanate:

The product is a free-flowing white powder having an NCO-content of 28% by weight (calculated 28.4% by weight) and a melting point of from 39° to 40° C.

II. Deactivating reaction of the solid adducts covered with liquid polyisocyanates by coating with polymer

1.4.1:

1.5 g of 4,4'-diamino-3,3'-dimethyl dicyclohexylmethane (DMDAD) are added to a suspension of 25 g of the covered polyisocyanate of Example 1.1.2 in 150 g of hexane. The equivalent ratio of diamine (DMDAD) to covering polyisocyanate (N) amounts to 0.5 equivalent of DMDAD to 1.0 equivalent of N. After stirring for 30 minutes at room temperature, the deactivated solid polyisocyanate is filtered off under suction and dried. The filtrate is substantially free from diamine. The polymer-coated, solid polyisocyanate is a free-flowing, colorless powder having a softening range of 118° to 122° C.

1.4.2 Production of a PU-forming reactive mixture:

9.0 g of the polyurea-covered product of Example 1.4.1 are stirred with 50 g of a linear, aromatic aminopolyether (AAPE), NH number 48.4. The mixture is stable in storage for months at room temperature. This system has a thickening point of 120° to 130° C., as determined on a sample.

1.4.3 Modified procedure for coating with polymer (diamine dissolved in polyether amine):

9.0. g of the adduct of TT and N described in Example 1.1.1 are mixed in 50 g of the aromatic aminopolyether AAPE (NH number 48.4) and 0.15 g of the diamine DMDAD added to the resulting mixture. A polymer coating is formed around the solid polyisocyanate particles. The mixture remains stable in storage for months at room temperature and has a thickending point of 115° to 120° C., as determined on a sample.

1.4.4 Modified procedure (addition of the covered polyisocyanates to a solution of diamine in aminopolyether):

The solid, finely divided covered polyisocyanates obtained in accordance with Examples 1.1, 1.2 and 1.3 are mixed with an aromatic aminopolyether AAPE (NH number 48.4) in which the following diamines (a), (b) or (c) had been dissolved in the quantities indicated as compounds (D) forming NCO-polymers with the covering polyisocyanates.

After storage for about 1 hour at room temperature, the respective thickening points of the reactive PU systems are determined.

| Formulations | a | b | c |
|---|---|---|---|
| Aminopolyether AAPE (NH number 48.4) | 50 g | 50 g | 50 g |
| Diamine | 0.2 g (DMDAD) | 0.05 g (ethylene diamine) | 0.10 g (diethylene triamine) |
| Polyisocyanate-covered polyisocyanate (according to Example) | 9 g (1.1.2) | 7 g (1.2.2) | 6 g (1.3.2) |
| Stability in storage at RT | stable | stable | stable |
| System thickening point | ~110° C. | 80–90° C. | 60–70° C. |

EXAMPLE 2

2.1 Process according to the invention 2.6 g of biuretized hexane diisocyanate (N) (21.3% NCO) are added to a suspension of 25 g of dimeric 2,4-diisocyanatotoluene (TT) in 150 g of hexane and the reaction mixture stirred for 30 minutes at room temperature. 1.5 of 3,3'-dimethyl-4,4'-diaminodicyclohexylmethane is then added to the polyisocyanate-covered, solid polyisocyanate. After 1 hour, the solid polyisocyanate thus polymer-modified (with a polyurea coating) is filtered under suction, washed with pretroleum and dried. Nor more aliphatic diamine can be detected in the filtrate (titration with 0.1 N HCl).

In order to determine the degree of deactivation, 17 g of the solid, polymer-coated polyisocyanate obtained are mixed with 100 g of an aromatic aminopolyether (AAPE), NH number 48.4, and the thickening point of the system determined: 85°–90° C.

The system applied in thin layers to textiles or solid substrates crosslinks in a few minutes at 120° C. to form an elastomeric polyurethane coating.

By contrast, the mixture remains stable in storage for at least several weeks at room temperature.

2.2 Comparison test based on the prior art—direct reaction of diamine with the surface of solid polyisocyanates This test is carried out in the absence of biuretized hexane diisocyanate (N). Working up and determination of the thickening point are carried out in the same way as in Example 2.1.

After the diisocyanate deactivated in accordance with the prior art by reaction of the diamine with the NCO-groups of the solid polyisocyanate particles themselves has been filtered under suction, 1.05 g of the aliphatic diamine (DMDAD) can still be determined in the filtrate (by HCl-titration). This means that about 26 mMoles of aliphatic diamine (DMDAD) have reacted off per mole of solid diisocyanate and the predominant proportion (approximately 70%) of the diamine is still present in free form in the solvent.

The modified polyisocyanate filtered under suction is washed with solvent and is now free from excess, unreacted aliphatic diamines (DMDAD).

In the test with aromatic aminopolyether (AAPE), a thickening point below 50° C. is measured. Even after standing overnight at room temperature, the mixture has thickened to such an extent that it can no longer be processed. This comparison test shows that the polymer coating according to the invention by means of a polyisocyanate applied by covering and subsequently reacted off with diamine to form a coating polymer is more effective and more complete than a deactivating reaction carried out on solid polyisocyanate particles in accordance with the prior art. The thin, effective deactivation coating according to the prior art leads to low system thickening points and to instability of the reactive PU mixture. Since, in the case of the polyisocyanates according to the prior art, the excess diamine was filtered off under suction with the solvent after the coating reaction, there is no longer any "self-healing effect", i.e. no increase in the thickening point, in the event of further reaction of the reactive PU mixture.

EXAMPLE 3

3.1 Covering reaction 3.2 parts of a 50% solution of a biuretized hexamethylene diisocyanate (N; NCO-content 21.3%) in toluene are run slowly with stirring into a suspension of 100 parts of finely divided (average particle size approx. 10 μm) 3,3'-diisocyanato-4,4'-dimethyl-N,N'-diphenylurea (TDIH) in 520 parts of hexane.

3.2 Polymer coating reaction

After intensive stirring for about 5 minutes, 1.92 parts of a 50% solution of 3,3'-dimethyl-4,4'-diaminodicyclohexylmethane (DMDAD) in toluene are added to the dispersion obtained in accordance with 3.1, followed by stirring for about 30 minutes. The urea diisocyanate (TDIH) protected by a polyurea covering (of N and DMDAD) is filtered under suction, washed with hexane and dried.

3.3 Reactive PU mixture 19 parts of the polymer-coated urea diisocyanate according to 3.2 are stirred with 100 parts of an aminopolyether (AAPE), NH number 48.4, to form a stable dispersion which remains stable in storage for a considerable period at room temperature. The reactive mixture has a systems thickening point of 80 to 90° C.

The carefully degassed reactive mixture (approx. 130 g) is poured into a flat, cold mold measuring 20×20 cm and heated for 4 hours in an oven (oven temperature 120° C.).

An approximately 3 mm thick elastomer test plate having the following mechanical properties is obtained:

| Surface hardness: | Shore A: | 93 | DIN 53 505 |
|---|---|---|---|
| | Shore D: | 42 | |
| Tensile strength | 13.8 MPa | | DIN 53 504 |
| Breaking elongation | 340% | | DIN 53 504 |
| Tear propagation resistance | 34.5 KN/m | | DIN 53 515 |
| Elasticity | 53% | | DIN 53 512 |

EXAMPLE 4

In situ production of a very finely divided, solid, stabilized polyisocyanate.

4.1 In situ production of a very finely divided polyisocyanate (TDIH)

174 g (1 mole) of 2,4-diisocyanatotoluene and 12.6 g (0.7 mole) of water are introduced into 800 ml of diisopropylether (DIP), followed by intensive stirring at room temperature. A gradually increasing evolution of $CO_2$ begins after a few minutes, the reaction mixture undergoing a gradual increase in temperature to approximately 35° C. The reaction mixture is heated by means of a water bath to 50° C. so that the reaction is over after a total of 2 hours (end of the evolution of $CO_2$; in all approximately 12 liters of $CO_2$ (uncorrected)).

A parallel test shows that the solvent still contains 0.02 mole of unreacted TDI. The isolated solid product has an NCO-content of 25.8% by weight.

4.2 Polymer covering of the TDIH

On completion of the reaction, first 4.44 g (0.02 mole) of isophorone diisocyanate (IPDI) and, after about 20 minutes, 9.52 g (0.04 mole) of diamine DMDAD dissolved in 20 ml of DIP are added to the dispersion of the TDIH which has accumulated in situ in very finely divided form (0.02 mole of diamine for the reaction with IPDI and 0.02 mole for binding the unreacted, free 2,4-diisocyanatotoluene still present in the solution). After stirring for about 2 hours at 40° C., the polymer-coated deposit of the solid TDIH is filtered under suction and dried at 50° C. in a vacuum drying cabinet. Yield: 163.4 g (93.3% of the theoretical), softening range 180°–190° C., NCO-content 22.5% by weight (theoretical 23.5% by weight taking the polymer coating into account).

4.3 Polymer-coated polyisocyanate dispersion in plasticizers and its use 400 ml of the dispersion—obtained from the production reaction—of the polymer-coated stabilized polyisocyanate in DIP (NCO-content 4.52% by weight) are mixed with 260 g of dioctyl phthalate plasticizer. The diisopropylether is then removed on a rotary evaporator. 326.4 g of a dispersion of the polymer-coated polyisocyanate (NCO-content 5.04% by weight) are obtained.

44.8 parts of this dispersion are mixed with 50 parts of the aminopolyether AAPE, NH number 48.4. The reactive PU mixture obtained does not undergo any increase in viscosity after storage for several months at room temperature. The thickening point of this system is 85° C.

For comparison, 20.6 g of non-stabilized, ground TDIH, (urea diisocyanate with an average particle diameter of approx. 10 μm), NCO-content 24.5% by weight, were dispersed in 79.4 parts of dioctyl phthalate. If this dispersion is subjected to the above stability test, an unstable reactive PU mixture is obtained, thickening in about 1 hour.

EXAMPLE 5

Use of the polymer-coated polyisocyanates for producing an elastomer 100 parts of the aromatic aminopolyether AAPE, NH number 48.4, are intensively mixed using a high speed stirrer with 20.1 parts of the polymer-coated solid diisocyanate produced in accordance with Example 4.2 (NCO:NH$_2$ index=1.25) to form a reactive PU suspension which is then degassed for about 15 minutes in a high vacuum.

A narrow strip of the reactive PU suspension obtained is applied to a Kofler bench. The minimum temperature at which elastic solidification occurs is measured after certain times.

| Time (mins.) | Elastic solidification at (°C.) |
|---|---|
| 3 | 85 or more |
| 5 | 82 or more |
| 10 | 80 or more |

The material is poured into a flat metal mold measuring 20 cm×20 cm×0.5 cm and hardened for 4 hours at 120° C.

An elastomer test plate having the following mechanical properties is obtained:

| | | |
|---|---|---|
| Tensile strength | 12.1 MPa | DIN 53 504 |
| Breaking elongation | 200% | DIN 53 504 |
| Tear propagation resistance | 26.4 KN/m | DIN 53 515 |
| Shore hardness according to DIN 53 505 | 92 A and 43 D | |
| Elasticity | 52% | DIN 53 512 |

EXAMPLE 6

Polymer coating stabilization in dependence upon the covering polyisocyanates and the reaction medium These examples show the extent to which the stabilization of a solid polyisocyanate (A) by the process according to the invention depends upon the chemical constitution, the solubility and the precipitation rate of the polyureas formed from the polyisocyanates (B) and the component (D) into various reaction media. These various stabilizing effects are clearly apparent from the following Table. The tests are carried out with the dimeric TDI (TT) as the finely divided, solid polyisocyanate (A) which is dispersed in 15 g of "solvent" and x g (cf. Table) of liquid polyisocyanate (B) and with a mixture of 0.68 g of diamine (DMDAD), 50 g of aromatic aminopolyether AAPE, NH number 48.4, and catalyst. The polymer-covered polyisocyanates dispersed in the solvents are produced in an NCO (from component B): NH$_2$ (from component (D) ratio of >1.

TABLE

Coating of TT with various polyisocyanates (B) in various solvents; state and thickening point of the reactive PU mixture

| Polyisocyanate (B) (in g) | Hexane | DIP | PPG Etherpolyol | Toluene | Dioctylphthalate |
|---|---|---|---|---|---|
| IPDI (x = 0.65 g) | liquid TP: 130-140° C. | liquid :140° C. | liquid :~150° C. | thickened (24 h) | thickened (24 h) |
| HDI (x = 0.48 g) | slightly thixotropic TP: 140-150° C. | liquid TP: ~150° C. | liquid ~160° C. | thickened — | thickened — |
| N (21.3% NCO) (x = 1.12 g) | liquid TP: 170° C. | liquid ~170° C. | liquid ~170° C. | thickened — | thickened — |
| HDI trim (21.7% NCO) (x = 1.1 g) | liquid TP: ~160° C. | liquid ~160° C. | liquid ~160° C. | thickened — | thickened — |
| HDI/dipropylene glycol 2:1 (x = 1.27 g) | liquid TP: ~110-120° C. | — | — | — | — |
| TDI/trimethylol propane (3:1) (x = 1.37 g) | liquid TP: ~100-110° C. | — | — | — | — |
| Comparison without | liquid TP: ~160° C. | liquid ~145° C. | liquid ~150° C. | liquid ~150° C. | liquid ~160° C. |

The Table shows the effect which the type and quantity of polyisocyanates (B) have upon the thickening behavior or system thickening point of the reactive PU mixture mentioned in dependence upon the solvent used.

For comparison, a reaction is carried out in which the polymer coating formed by the separately added polyisocyanate (B) is left out (state-of-the-art process). The system thickening point is shown under T.P. in the Table. In the event of inadequate stabilization, the reactive mixture thickens immediately and can no longer be processed.

As can be seen from the Table, solvents of relatively high polarity which have too good a dissolving effect on the polyisocyanate (B) and which, hence, do not lead to covering of the polyisocyanate (A) (TT in the present case), are unsuitable.

The aliphatic diisocyanates and, in particular, aliphatic polyisocyanates effectively stabilize (i.e. retard the reactivity of) the solid polyisocyanates in accordance with the invention through the formation of a polymer coating.

EXAMPLE 7

Time-dependent stabilizing effect in the polyisocyanate covering reaction 7.1 Polyisocyanate covering reaction—brief 1.3 g of isophorone diisocyanate (IPDI) are added to a suspension of 17 g of dimeric TDI (TT) in 30 g of dioctylphthalate. Immediately afterwards (3 minutes), 1.3 g of diamine (DMDAD) and 100 g of the aromatic aminopolyether AAPE (NH number 48.4) are stirred in. The thickening point of this reactive PU mixture is below 50° C. After the reactive mixture has stood for several hours at room temperature, it thickens to a considerable extent.

7.2 Polyisocyanate covering reaction—after standing

If, by contrast, 1.3 g of diamine DMDAD and 100 g of aromatic aminopolyether AAPE are added to the above-mentioned suspensions of TT in dioctylphthalate and IPDI after a period of 2 to 3 hours, a mixture stable in storage at room temperature is obtained and has a system thickening point of 70° to 75° C. This mixture shows slightly thixotropic behavior after prolonged standing.

This result may be interpreted to mean that the solid polyisocyanate (TT) interacts (through adsorption or absorption) only gradually with the liquid IPDI, producing a time-dependent covering reaction of the TT-particles. The diamine DMDAD added then produces the polyurea responsible for deactivation of the mixture on the surface of the solid polyisocyanate particles.

The above time effect is generally only pronounced when a (low molecular weight) diisocyanate (B), such as for example HDI or IPDI or TDI, and a relatively polar solvent, such as toluene or dioctylphthalate, are used in the polyisocyanate covering reaction.

EXAMPLE 8

The following tests were carried out to confirm the fact that polyurea formed during the external reaction of a polyisocyanate (B) and a component (D) in the presence of a solid, finely divided polyisocyanate (A) is based on a surface covering of the solid polyisocyanate (A) and, more particularly, the fact that the resulting deactivation is obtained without any co-reaction of the solid polyisocyanate with the diamine. 3,3'-dimethyl-4,4'-diaminodicyclohexylmethane (DMDAD) was used as the aliphatic diamine and a biuret polyisocyanate of hexane diisocyanate (N), NCO content approx. 21.3%, as the polyisocyanate (B).

8.1 Process according to the invention

The following starting components are mixed in the order indicated and the thickening point of the reactive mixture is determined as a measure of its stability in storage.

15 g of a linear polypropylene glycol (OH number 56), 9.0 g of dimeric 2,4-TDI (TT) and 0.34 g of biuretized hexane diisocyanate (N) are stirred for 30 minutes and then with 0.2 g of diamine DMDAD, 50 g of aromatic aminopolyether (AAPE), NH number 48.4, and 0.05 g of an approximately 57% solution of Pb octoate in ligroin.

The thickening point of this mixture is in the range from 130° to 140° C. (as determined after storage for 1 hour at room temperature after mixing).

8.2 Comparison test

The procedure was as in Example 8.1, except that the 0.32 g of polyisocyanate (B) (N) was not added. The mixture obtained has a thickening point of 85° to 90° C. which is distinctly lower than the thickening point of the mixture obtained by the process according to the invention (8.1).

This result is a clear indication that the distinctly increased deactivation of the sokid polyisocyanate observed in Example 8.1 in relation to the aromatic NH$_2$-groups in the aminopolyether cannot be explained by the fact that an aliquot part of the component (D) reacts uniformly both with the polyisocyanate present in liquid phase (polyisocyanate (B) and the polyisocyanate present in heterogeneous, finely divided solid phase (polyisocyanate (A). If this were the case, the thickening point (i.e. stability in storage) of the mixture obtained by the process according to the invention (Example 8.1) would be distinctly below that of the mixture produced by method (B).

Due to the competitive reaction of the aliphatic diamine with the polyisocyanate (B) containing NCO-groups, the concentration of amine would also be lower in any event than described in Example 8.2, resulting in weaker stabilization of the solid polyisocyanate than in Example 8.2. The distinctly increased stabilizing effect obtained in accordance with Example 8.1 according to the invention is explained by the fact that the polyurea of the diamine (D) and the liquid NCO-biuret polyisocyanate (B) formed on the particle surface of the solid polyisocyanate (A) has a much stronger screening effect than the polyurea formed in accordance with Comparison Example 8.2 from the diamine and the solid polyisocyanate (A) alone.

EXAMPLE 9

Changing the NCO:NH$_2$-ratio of polyisocyanate (B) to compound (D)

Various reaction mixtures are produced by the process according to the invention (Example 8), the molar ratio of NCO from the biuret polyisocyanate (B) to NH$_2$ in the diamine (D) covering an equivalent ratio of (B) to (D) of from 0 to 2.05. By contrast, the quantity of diamine (D) (DMDAD) added remains constant whereas the quantity of the biuret polyisocyanate (B) is varied accordingly.

| Quantity of biuret polyisocyanate (B) added (g) | NCO(B):NH$_2$ (D) ratio (equivalent) | System thickening point (°C.) |
|---|---|---|
| 0 | 0 | 90 |
| 0.09 | 0.28 | 95–100 |
| 0.17 | 0.51 | 105–110 |
| 0.26 | 0.79 | 125–130 |
| 0.33 | 1.00 | 130–140 |
| 0.43 | 1.28 | 130–140 |
| 0.51 | 1.54 | 130–140 |
| 0.60 | 1.81 | 130–140 |
| 0.68 | 2.05 | 130–140 |

It can be seen that the thickening point is distinctly influenced with increasing addition of biuret polyisocyanate (B) until the equivalent point is reached (molar ratio of NCO(B) : NH$_2$ (D)=1:1), because the quantity of polyurea responsible for deactivation of the solid polyisocyanate (A) increases in that range. The optimal deactivation of the solid polyisocyanate (A) is reached after the equivalent point is reached, so that larger additions of the NCO-biuret polyisocyanate (B) have no further effect on the thickening point of the system.

EXAMPLE 10

Stabilization of a polyisocyanate by covering with polyurea (variation of the diamines)

10.1

In the following reaction mixtures, the amine components (D) are varied for the same isocyanate component (IPDI). The NCO:NH$_2$ ratio (diisocyanate (B) to aliphatic diamine (D)) remains at approximately 1. The polyurea covering formed from the diisocyanate (B) and the amines (D) on the particle surface of the solid polyisocyanate (A) leads to entirely adequate deactivation of the solid polyisocyanate with respect to active hydrogen compounds of the type used in the production of polyurethanes. The mixtures remain stable in storage for several months at room temperature. Reaction mixture:

25 g of linear polypropylene glycolether (PPG-ether), OH number 56

18 g of dimeric TDI (TT) (suspension of TT in PPG 0.68 g of IPDI (stirred into suspension, reacted after 10 min. with x g of diamine (D) (equivalent quantities to IPDI)

After 1 hour at room temperature, a solution of 25 g of linear PPG-ether (see above), 4.5 g of 3,5-diethyl-2,4- :-2,6(65:35)-diaminotoluene (DETA) and 0.5 g of Pb octoate solution (as described above in Example 8.1) is added to the mixture.

The diamines or polyamines (D) listed in the following Table are used as the diamines:

| Diamine (D) | Quantity x) (g) | System thickening point (°C.) |
| --- | --- | --- |
| Ethylene diamine | 0.18 | 110° C. |
| Diethylene triamine | 0.29 | 120° C. |
| 2,5-diamino-2,5-dimethyl hexane | 0.4 | 110° C. |
| Isophorone diamine | 0.98 | 125° C. |
| DMDAD | 0.64 | 125° C. |

The reaction mixtures are solidified above the thickening point and form highly elastic polyurethane moldings having mechanical properties in the following ranges:

| Hardness (Shore A) | 90–92 |
| --- | --- |
| Tensile strength (MPa) | 8.9–10 |
| Breaking elongation (%) | 200–240 |
| Tear propagation resistance (KN/m) | 14–18 |
| Elasticity (%) | 53–55 |

EXAMPLE 11

In this example, a trimeric hexane diisocyanate (NCO-content 21.6%) is used instead of IPDI and tested in combination with various diamines or polyamines (D) in the following reaction mixtures;

Reaction mixture:

15 g of linear PPG-ether, OH number 56

9.0 g of dimeric 2,4-TDI (TT)

1.3 g of trimeric 1,6-diisocyanatohexane (HDI-trim)

x g of amines (D)

50 g of aromatic aminopolyether (AAPE), NH-number 48.4

0.5 g of solution of lead octoate in cleaning spirit

| Amines (D) | Quantity x (g) | System thickening point (°C.) |
| --- | --- | --- |
| Ethylene diamine | 0.18 | 80 |
| Diethylene triamine | 0.28 | 95 |
| 2,5-diamino-2,5-dimethyl hexane | 0.40 | 100 |
| IPDA | 0.48 | 90 |
| DMDAD | 0.69 | 95 |

If, after brief degassing in vacuo, the liquid one-component reactive PU systems (readily processible at room temperature) are heated to 110°–120° C. in a mold coated with a silicone-release agent, a highly elastic PU elastomer having the following mechanical properties is obtained after 1 to 2 hours. (The mechanical properties are substantially unaffected by the nature of the stabilization.)

| Hardness (Shore A): | 92 |
| --- | --- |
| Tensile strength (MPa): | 18.5 |
| Breaking elongation (%): | 420 |
| Tear propagation resistance (KN/m): | 39.2 |
| Elasticity (%): | 60 |

EXAMPLE 12

(Stabilization of a solid polyisocyanate by covering with polyadduct)

1.2 g of a biuretized hexane diisocyanate (N) are added to a suspension of 9 g of dimeric TDI (TT) in 15 g of a linear polypropylene glycol ether (molecular weight 2000). After a short time, the compounds indicated below are added with stirring in that order. 50 g of a linear aromatic aminopolyether (AAPE), NH number 48.4, are then added. After standing for 1 hour, the thickening point of the system is determined.

| Compound (D) | Quantity (g) | Thickening point (°C.) |
| --- | --- | --- |
| 1,2-dimethyl tetrahydro-pyrimidine | 0.3 | 100° C. |
| 1,5-diazabicyclo-(4,3,0)-non-5-ene | 0.32 | 110° C. |
| Tetramethyl guanidine | 0.3 | 100° C. |
| Hydrazine hydrate | 0.2 | 70° C. |
| β-semicarbazidopropionic acid hydrazide (H$_2$N—NH—CO—NH—CH$_2$—CH$_2$—CO—NH—NH$_2$) | 0.45 | 70° C. |

EXAMPLE 13

Influencing the stability in storage (thickening point) of a one-component reactive PU system by the addition of free isocyanates

13.1 Process according to the invention

The starting components indicated below are mixed in that order and the thickening point determined after storage for 1 hour as a measure of the stability in storage of the reactive PU mixture.

30 g of linear PPG-ether, OH number 56
22 g of dimeric TDI (TT) (suspension)
0.55 g of biuretized HDI (N) (NCO=21.3%) (mixed into suspension)
0.2 g of DMDAD and
100 g of aromatic aminopolyether (AAPE), NH number 48.5 were mixed in after 30 minutes,
0.1 g of Pb octoate solution (cf. Example 8.1) added.

The thickening point of the reactive PU mixture is 100° C.

13.2 Comparison Test (stabilization not by covering with polyisocyanates (B), but instead solely by reaction of the solid polyisocyanates (A) with aliphatic diamines)

A thickening point comparable with that obtained in Example 13.1 was adjusted by slightly altering the addition (i.e. quantity added) of aliphatic diamines:

30 g of PPG-ether, OH number 56
22 g of dimeric TDI (TT)
0.3 g of diamine (DMDAD)
100 g of aromatic aminopolyether (AAPE), NH number 48.4
0.1 g of Pb octoate solution (cf. Example 8.1).

The thickening point of this system is 103° C.

If free isocyanates (2,4-TDI) are added to the one-component reactive system obtained in accordance with Examples 13.1 and 13.2, the following changes in the thickening points are observed for the various quantities added:

| Process | Addition of 2,4-TDI in g/150 g of one-component mixture | | | | |
|---|---|---|---|---|---|
| | 0 | 0.2 | 0.3 | 0.4 | 0.6 |
| 13.1 According to the invention | 100 | 95 | 90 | 80 | 85 |
| 13.2 State of the art | 103 | 60 | 50 | unstable in storage | |

Whereas the one-component reactive system produced by the process according to the invention (Example 13.1) remains stable in storage following the addition of 0.6 g of 2,4-TDI per 150 g of mixture and shows only a slight change in its thickening point, the reactive mixture produced for comparison (Example 13.2) is significantly affected by the addition of only 0.3 g of TDI. This mixture, which has a thickening point of 50° C., is not stable in storage and, after a few days, can no longer be processed.

EXAMPLE 14

Modification of the one-component system by the subsequent addition of free isocyanate (pre-extending reactions in one-component systems)

14.1 Process according to the invention 0.64 g of a biuretized polyisocyanate (N), 21.3% NCO, and—shortly afterwards—0.4 g of diamine (DMDAD) are added to a suspension of 30 g of a linear polypropylene glycol ether (OH number 56) and 15 g of dimeric TDI (TT). This is followed by the addition of 100 g of an aromatic aminopolyether, NH number 41.5 (molecular weight accordingly approx. 2400), and 0.1 g of a 57% solution of Pb (II)-2-ethylhexanoate in cleaning spirit. A viscosity of 10,000 to 12,000 mPa.s at room temperature is obtained. In order now to pre-extend the aminopolyether into an aminopolyether of relatively high molecular weight, 3.6 g of 2,4-TDI are introduced into the reaction mixture. The reaction mixture gradually thickens (through reaction of the free TDI with aminopolyether) and a plastic, highly viscous system of paste-like consistency is obtained after a few hours. It is stable in storage at room temperature and may be thermally crosslinked at any time at temperatures of 110° to 130° C. to form a highly elastic polyurethane material.

14.2 Comparison Test

The individual components are added in the same order as in Example 14.1; the only difference is that no biuret polyisocyanate (N) is used. After the addition of 3.6 g of 2,4-TDI, a highly viscous preadduct is again obtained, but on this occasion is not stable in storage at room temperature. After only one day, the mixture has thickened to such an extent that it can no longer be processed under normal conditions.

EXAMPLE 15

Behavior of the thickening point in reactive polyurethane systems in the production of moldings of high volume

15.1 Process according to the invention 90 g of dimeric TDI (TT) are dispersed in 100 g of a linear polypropylene glycol ether (molecular weight 2000) and 1.2 g of biuretized HDI (N) added to and mixed with the resulting dispersion. After 30 minutes, a mixture of 0.8 g of diamine DMDAD, 500 g of the aromatic aminopolyether AAPE, NH number=48.4, and 0.5 g of lead octoate solution (cf. Example 8.1) is incorporated in the mixture. The reactive PU mixture is stable in storage at room temperature and has a thickening point of 100° C. The reaction mixture is poured completely into a 1 liter metal can (diameter 12 cm, height 10 cm) and stored in a heating cabinet within an internal temperature of 120° C. The solidification of the reaction mixture progresses inwards with increasing temperature.

During the gradual increase in temperature of the reaction mixture, samples are taken from the inner, still liquid constituents of the hardening reaction mixture after the periods indicated and their respective thickening points separately determined.

| Time/hours | Temperature of the liquid core | Thickening point (°C.) |
|---|---|---|
| 0 | room temperature | 100 |
| ½ | 40 | 105 |
| 1 | 60 | 100 |
| 2 | 75 | 105 |
| 4 | 85 | 105 |

As the Table shows, the thickening point of the mixture according to the invention shows hardly any change during the solidification phase. After 6 to 8 hours, the reaction mixture has completely solidified and, after removal from the mold, the test specimen shows a smooth, undamaged outer skin and a uniform structure throughout its cross-section.

15.2 Comparison Test

This procedure is as described above, but without the addition of biuretized HDI (N). In this case, a polymer coating is formed on the surface of the solid polyisocyanate (TT) itself through reaction of the diamine DMDAD with the isocyanate groups.

The thickening point of this reactive system is 90° C. Under the conditions described in the foregoing for formation of the molding and heating, the following thickening points are measured on samples of the liquid core:

| Time/hours | Temperature of the liquid core | Thickening point (°C.) |
|---|---|---|
| 0 | room temperature | 90 |
| ½ | 40 | 95 |
| 1 | 60 | 110 |
| 2 | 75 | 125 |

The thickening point of the reaction mixture undergoes a distinct change during solidification from the peripheral zones. During the heating phase, the free aliphatic diamine still present in the reaction mixture enters into a further reaction with the solid polyisocyanate, so that the thickening point increases continuously with slowly increasing temperature. The inner core of the sample still remains liquid for a long time, even after external solidification of the mixture. When the temperature is further increased, the outer, already solidified crust bursts open through thermal expansion of the liquid, i.e. as yet unsolidified, material at any weak spots present, so that liquid material flows out at those places. Thereafter solidification gradually occurs with increasing temperature and the molding obtained, apart from stress cracks, shows a completely scarred surface.

EXAMPLE 16

16.1 Production of the polymer-coated polyisocyanate

A solution of 46.2 g of an NCO-prepolymer of 2 moles of 2,4-tolylene diisocyanate and 1 mole of trimethylol propane (NCO content=17.5%) in 92 g of ethyl glycol ether acetate is run slowly with stirring at room temperature into a suspension of 200 g of finely divided (average particle size approx. 10 μm) 3,3'-diisocyanato-4,4'-dimethyl-N,N'-diphenylurea (TDIH) in 1400 ml of n-hexane. After intensive stirring for 5 minutes, the NCO-prepolymer added has precipitated onto the solid TDIH. A solution of 19.04 g of diamine DMDAD in 100 ml of n-hexane is run with stirring into the TDIH thus covered, followed by stirring for 4 hours at 40° C. The TDIH protected by polyurea covering is filtered off under suction, washed and dried.

16.2 Reactive PU systems using an aliphatic polyether diamine 16.2.1 Pre-extension of the diamine: 4.44 parts of 1-isocyanato-3-isocyanatomethyl-3,5,5-trimethylcyclohexane (IPDI) are run with intensive stirring into 100 parts of a polyoxypropylene ether diamine containing aliphatic NH$_2$-groups (molecular weight 2000) (Jeffamine ®, D-2000, a Texaco product). After degassing for 1 hour at 90° C., a polyoxypropylene ether diamine is obtained with an increased average molecular weight of 3777 and a viscosity of 26,000 mPa.s at 22° C.

16.2.2 Reactive PU mixture (according to the invention): 15 parts of 2,4-:-2,6-(65:35)-diamino-3,5-diethyltoluene (DETA) are added to this pre-extended polyoxypropylene ether diamine and 55 parts of the polymer-coated diisocyanate stabilized by the method described above (Example 16.1) are suspended in the resulting mixture. After degassing at 50° C., a suspension stable in storage at temperatures of up to 50° C. and having a viscosity of 300,000 mPa.s at 22° C. is obtained. The reactive PU mixture is stable in storage at room temperature. The thickening temperature of the reactive PU system is 92° C. An elastomer sample produced from the reactive PU suspension by heating has a Shore D hardness of 62.

16.3 Use of the reactive PU mixture as a reactive adhesive

The thermosetting mixture which is stable at room temperature and sets quickly at elevated temperature may be used as a reactive polyurea adhesive which shows high stability in storage at room temperature and a spontaneous increase in viscosity at relatively low heating temperatures, accompanied by rapid hardening, and improved adhesion properties, even at elevated temperatures.

16.3.1 Test for determining the shear strength of bonds: The test material used consisted of 20 mm×40 mm×4 mm strips of a polyester resin reinforced with 30% of glass fibers (SMC) and iron plates measuring 20 mm×40 mm×2 mm which, before application of the adhesive, had been coated with a number 280 abrasive paper.

The strips are preheated to 120° C. After application of the adhesive in a layer thickness of 0.2 mm, two strips are placed together in such a way that an overlapped area of 10×20 mm is formed. These test specimens are stored at 120° C. for the period indicated below. Immediately afterwards, they are manually tested for shear strength which, at 1N/mm$^2$ without separation of the bond, is high enough for the test specimens to be handled for further processing. After the test specimens have been stored for 1 hour at room temperature, their shear strength is determined in accordance with DIN 53 283 (spindle advance 100 mm per minute).

16.3.2 Results: The results are shown in the following Table for bonding to glass-fiber-reinforced polyester resins and to iron. After 15 minutes at 120° C., the shear strengths were measured first immediately, i.e. by hand while the test specimens were still hot (see first column), and after the bond had been stored for 1 hour at room temperature (see other columns).

TABLE

| Adhesive mixture according to Example No. | Shear strength [N/mm$^2$] after 15 mins./120° C. immediately (tested by hand while still hot) | | Shear strength [N/mm$^2$] after 15 mins./120° C. and after storage (for 1 hour at room temperature) | |
|---|---|---|---|---|
| | SMC | iron | SMC | iron |
| 16 | >1 | >1 | 9.5 | 15.0 |

EXAMPLE 17

Use of polymer-coated polyisocyanates for the production of one-component polyurethane elastomers 111 g of IPDI are dissolved in 2000 g of a linear polypropylene glycol ether having a molecular weight of 2000. After stirring for 40 hours at 130° C., followed by degassing, a pre-extended polyether diol having a molecular weight of 4222 and a viscosity of 3100 mPa.s at room temperature is obtained.

14.8 g of dimerized TDI (TT) are suspended in 100 g of this diol and 1.59 g of biuretized HDI (N) subsequently added to the resulting suspension. After intensive stirring for 5 minutes, the biuret polyisocyanate added has precipitated onto the solid diisocyanate in the form of a covering. 0.43 g of diethylene glycol is then stirred in, followed by stirring for 30 minutes at room temperature. After the addition of 2.5 g of 2,4-:2,6-(65:35)-diamino-3,5-diethyl toluene isomer mixture (DETA) and 0.2 g of lead octoate solution (see Example 8.1), the whole is degassed for 1 hour at 40° C. A suspension is obtained which is highly stable in storage at up to 40° C. and which has a viscosity of 7000 mPa.s at 20° C. and a thickening point of 64° C. After solidification and tempering for 2 hours at 120° C., an opaque elastomer having the following properties is obtained:

| | | |
|---|---|---|
| Tensile strength (MPa) | 4.5 | DIN 53 504 |
| Breaking elongation (%) | 200 | DIN 53 504 |
| Tear propagation resistance (KN/m) | 8 | DIN 53 515 |
| Shore hardness (A) | 62 | DIN 53 505 |
| Elasticity (%) | 34 | DIN 53 512 |

EXAMPLE 18

Use in the production of polyurethane elastomers based on aromatic and aliphatic aminopolyethers 2.0 parts of a biuret polyisocyanate (N) (21.5 NCO) are emulsified in 100 parts of an aromatic aminopolyether based on a polyoxypropylene ether diol (molecular weight 2000)/2,4-tolylene diisocyanate (molar ratio 1:2) produced in accordance with German Offenlegungsschrift No. 2,948,419 (amine number 48.4, molecular weight 2334). 26.3 parts of dimeric TDI (TT) are suspended in the resulting emulsion, the droplets of the biuret polyisocyanate (N) precipitating onto the solid, finely divided dimeric TDI in the form of a surface covering. 1.2 parts of 4,4'-diamino-3,3'-dimethyl dicyclohexylmethane (DMDAD) are then added, followed by stirring for 2 hours at 40° C. to form the polyurea polymer covering. Finally, 100 parts of an aliphatic aminopolyether obtained by reacting 100 parts of a polyoxypropylene ether diamine having a molecular weight of 2000 (Jeffamine, D-2000, a Texaco product, aliphatic terminal amino groups) with 5.55 parts of isophorone diisocyanate are added.

A one-component casting mixture is obtained which shows high stability in storage at up to 50° C. and which has a thickening temperature of 86° C. and a viscosity of 20,000 mPa.s at 22° C. After solidification and tempering for 8 hours at 120° C., a high-quality elastomer having the following mechanical properties is obtained:

| | | |
|---|---|---|
| Tensile strength (MPa) | 12 | DIN 53 504 |
| Breaking elongation (%) | 600 | DIN 53 504 |
| Tear propagation resistance (KN/m) | 29 | DIN 53 515 |
| Shore Hardness A | 77 | DIN 53 505 |
| Elasticity (%) | 42 | DIN 53 512 |

EXAMPLE 19

Dependence of the thickening temperature upon the quantity of foreign polymer coating 19.1 Process according to the invention In the following reaction mixture, the quantity of polymer deposited on the finely divided, solid, dimeric tolylene diisocyanate is varied by varying the quantity of the aliphatic polyisocyanate (N) and the aliphatic diamine (DMDAD) in the manner indicated. The $NCO:NH_2$ ratio of the two components producing the polymer coating was kept at about 1.1:1, i.e. the isocyanate is always present in a slight excess.

Mixture:
| | |
|---|---|
| 15 g | of a linear polypropylene glycol ether, (PPG) molecular weight 2000 |
| 9 g | of dimeric TDI (TT) (suspension of TT in PPG) |
| x g | of biuretized HDI (N) (added to suspension) |
| y g | of diamine (DMDAD) |
| 50 g | of an aromatic aminopolyether (AAPE), NH number 48.4) (mixed in after 30 minutes) |
| 0.05 g | of lead octoate solution in cleaning spirit (cf. Example 8.1 added to composition). |

The thickening points (measured after 1 hour) of the reactive PU system are as follows:

| Reaction components for the polymer coating | | |
|---|---|---|
| x (g) biuretized HDI (N) | y (g) diamine (DMDAD) | Thickening point (°C.) |
| 0.1 | 0.05 | 70 |
| 0.18 | 0.10 | 95 |
| 0.27 | 0.15 | 135 |
| 0.35 | 0.20 | 140 |
| 0.52 | 0.30 | 140 |
| 0.85 | 0.50 | 142 |

Even small additions of the two components N and DMDAD are sufficient to make the reactive mixtures adequately stable in storage at room temperature (system thickening point approx. 70° C. and 95° C.) through the polymer coating. Beyond a certain concentration limit of both components, the thickening point of the reaction mixture shows virtually no further change. The coating formed appears adequate for stabilization.

19.2 Comparison Test (no foreign polymer coating)

For comparison, the dependence of the thickening point of a similar, state-of-the-art reactive system is tested by directly carrying out a polyurea-forming reaction with the diamine (DMDAD) added on the surface of the solid dimeric diisocyanate (TT) in accordance with the prior art instead of covering the finely divided solid diisocyanate (TDI). The composition of the mixture is the same as in Example 19.1, except that the biuretized HDI (N), i.e. the covering foreign polyisocyanate, is not added. The results obtained are shown in the following Table.

| y g of diamine DMDAD | Thickening point (°C.) |
| --- | --- |
| 0 | after thickening for about 15 minutes |
| 0.05 | 50° C. after thickening for about 1 hour |
| 0.1 | 65 |
| 0.15 | 75 |
| 0.20 | 90 |
| 0.30 | 100 |
| 0.50 | 130 |

It can clearly be seen that the deactivating effect increases with increasing quantity of the aliphatic diamine. Accordingly, stability in storage is directly proportional to the quantity of diamine added.

EXAMPLE 20

A solution of 7.8 g of biuretized HDI (N) in 5 g of toluene is added dropwise at room temperature to a suspension of 100 g of dimeric tolylene diisocyanate (TT) in 100 g of hexane. After stirring for 30 minutes, 4.5 g of the aliphatic diamine (DMDAD) are added. After 1 hour, the suspension is filtered under suction giving 108.5 g of the finely divided TT covered with biuretized HDI.

36 g of this polyisocyanate-covered product are stirred into a melt of a linear polyester diol (molecular weight 2000) of adipic acid and ethylene glycol at 50° to 60° C. After 0.4 g of Formrez UL-29 (an S-containing Sn catalyst produced by Witco (USA)) are added and mixed in, the melt is left to cool.

The melt may be granulated by a suitable grinding process. The reactive mixture, which is stable in storage at room temperature, may be remelted at any time, introduced into a suitable mold and hardened by heat shock at 120° to 130° C. After mold release, a highly elastic polyurethane having the following mechanical properties is obtained:

| | |
| --- | --- |
| Hardness (Shore A) | 82 |
| Tensile strength (MPa) | 36.5 |
| Breaking elongation (%) | 780 |
| Tear propagation resistance (KN/m) | 52 |
| Elasticity (%) | 58 |

EXAMPLE 21

21.1 Polyisocyanate-covered MDI dimer 2 g of biuretized 1,6-diisocyanatohexane (N) are added with stirring to a suspension of 20 g of a low molecular weight, dimeric 4,4'-diisocyanatodiphenylmethane (produced in accordance with European Pat. No. 71 898 by the complete dimerization of MDI) in 50 g of diisopropyl ether. After 1 hour, the solid product is filtered under suction. 21.75% of a powder of the covered polyisocyanate having an NCO-content of 17.85% are obtained.

21.2 Polymer-coated MDI-dimer 20 g of the polyisocyanate-covered MDI-dimer (Example 21.1) are added to and homogeneously mixed with a solution of 0.15 g of DMDAD in 100 g of an aromatic polyether amine. After 1 hour, the suspension has a thickening point of 95° C. The reactive mixture is stable in storage at room temperature, but solidifies after a short time at 120° to 130° C. to form a highly elastic polyurethane elastomer.

EXAMPLE 22

1.0 g of biuretized hexane diisocyanate (Desmodur-N, a product of Bayer AG) is stirred into a suspension of 17.4 g of dimeric tolylene diisocyanate in 100 g of a polyoxypropylene ether diol having a molecular weight of 2000. After about 30 minutes, 0.16 g of ethylene glycol is added. After another 30 minutes, 5.0 g of 2,4-diamino-3,5-diethyl toluene and 0.1 g of lead octoate are added to the mixture. The viscosity of the reaction mixture remains stable at room temperature. A distinct increase in viscosity (thickening through polyurea formation from the dimeric TDI and the aromatic diamine) only occurs at elevated temperature, for example 75° C. The thickening point as determined on a Kofler bench is 70° C.

If 0.28 g of diethylene glycol is used instead of 0.16 g of ethylene glycol, a thickening point of 60°-65° C. is observed under the described conditions, i.e. this mixture is also stable in storage at room temperature.

EXAMPLE 23

23.1 Preparation of an urethane-modified polyol 154 g of dimeric toluylene-diisocyanate (TT) (0,885 NCO-equivalents) are suspended in a mixture of 670 g of a polyoxypropylene ether diol having a molecular weight of 1000 (1,34 OH-equivalents), 300 g of a polyoxypropylene ether triol having a molecular weight of 450 (2,00 OH-equivalents), 30 g of ethylene glycol (0,968 OH-equivalents) and 0,5 g lead-(II)-bis-ethylhexanoate (24% Pb in the catalyst) at ambient temperature, and the suspension is heated to 120° C. with stirring. The dimeric toluylene-2,4-diisocyanate passes into solution and reacts fully with the polyol mixture within a few minutes (JR-detection, viscosity increase).

After degassing for 2 hours at 90° C. a slightly opaque, urethane-modified polyol mixture having a viscosity of 35 mPa.s at 22° C. and 500 mPa.s at 70° C. is obtained.

Instead of dimeric toluylenediisocyanate an equivalent quantity (110,6 g; 0,885 NCO-equivalents) of 4,4'-diisocyanato-diphenylmethane (MDI) can be used alternatively.

23.2 Covering of TT with a foreign polymer (from biuretisized hexane diisocyanate and 4,4'-diamino-3,3'-dimethyl-dicyclohexane) in situ within the urethane modified polyol 23.1

684 g (3,93 NCO-equivalents) of dimeric toluylene-2,4-diisocyanate (TT) are suspended in the urethane-modified polyol 23.1 at ambient temperature. After 15 minutes of stirring 17,3 g (0,087 NCO-equivalents of Desmodur ®N (BAYER AG-Leverkusen, D-5090) are emulgated in the suspension. The emulgated Desmodur N (biuretisized hexane-1,6-diisocyanate) deposits on the surface of the solid, finely suspended TT-particles. 10 minutes after that addition are added 10,0 g (0,084 NH₂-equivalents) of 4,4'-diamino-3,3'-dimethyl-dicyclohexylmethane, forming the polymer coating. After 30 minutes of stirring the suspension is degassed during 1 hour at 50° C. and a room temperature stable one-component-PU-adhesive mixture (viscosity 100 Pa.s at 23° C.) is obtained. The adhesive mixture hardens quickly at temperatures of 100° to 130° C. to a tough-elastic, hard polyurethane.

What is claimed is:

1. A process for the production of solid polyisocyanates stabilized by a polymer coating and showing retarded reactivity comprising:

(I) mixing
- (A) at least one solid polyisocyanate in particulate form, said solid polyisocyanate (A) having a melting point above 38° C., with
- (B) at least one polyisocyanate having a composition different from that of component (A) in quantities of from 0.05 to 50 parts by weight of (B) per 100 parts by weight of (A), said polyisocyanate (B) being in a form capable of covering the particles of component (A), wherein said mixing is conducted at a temperature below the melting point of component (A) and results in the covering of the particles of component (A) by component (B), and (II) reacting the resultant covered product suspended in
- (C) a component selected from the group consisting of
  - (i) inert, weakly polar organic solvents
  - (ii) plasticizers,
  - (iii) organic compounds containing two or more hydroxyl groups and having molecular weights of from 400 to 6000,
  - (iv) organic compounds containing two or more aromatically bound amino groups and having molecular weights of from 400 to 6000, and
  - (v) mixtures thereof with,
- (D) at least one component selected from the group consisting of
  - (i) compounds containing one or more hydrogen atoms capable of reacting with isocyanate groups,
  - (ii) compounds containing no hydrogen atoms capable of reacting with isocyanate groups but which are capable of forming polymers with isocyanates, and
  - (iii) mixtures thereof, provided that component (D) cannot be of the type included within the definition of component (C), wherein said reaction results in the coating of component (A) by a polymer formed by the reaction of components (B) and (D).

2. The process of claim 1 wherein component (B) is liquid, oily or resinous.

3. The process of claim 1 wherein either component (A) and/or component (B) are suspended in component (C) prior to the mixing step (I).

4. The process of claim 1, characterized in that aliphatic or cycloaliphatic difunctional and/or higher polyisocyanates or polyol-modified polyisocyanates or NCO-prepolymers based on relatively high molecular weight polyhydroxyl compounds are used as the polyisocyanates (B).

5. The process of claim 1, characterized in that from 0.2 to 25 parts of polyisocyanate (B) to 100 parts of finely divided polyisocyanate (A) are used.

6. The process of claim 1, characterized in that dimeric or trimeric diisocyanates or urea diisocyanates, having particle sizes of from 0.5 to 200 μm are used as the finely divided polyisocyanates (A).

7. The process of claim 1, characterized in that the compounds (D) are selected from the group consisting of
- (i) aliphatic or cycloaliphatic diamines or polyamines,
- (ii) hydrazine, alkyl hydrazines, N,N'-dialkyl hydrazines and di- or polyhydrazide compounds,
- (iii) monofunctional or bifunctional amidines or guanidines containing one or two NCO-reactive hydrogen atoms
- (iv) acyclic, monocyclic or bicyclic amidines or guanidines free from NCO-reactive hydrogen atoms, and
- (v) mixtures thereof.

8. Polymer-coated, finely divided polyisocyanates of retarded reactivity produced by the process of claim 1.

9. In the process for producing polyurethanes or polyureas from
- (A) polyisocyanates,
- (B) relatively high molecular weight polyhydroxyl and/or polyamine compounds,
- (C) optionally, low molecular weight chain extending agents,
- (D) optionally, catalysts, and
- (E) optionally other auxiliaries and additives, the improvement wherein said component (A) and optionally components (B) and/or (C) are supplied in the form of the product produced according to the process of claim 1.

* * * * *